US009701732B2

(12) United States Patent
Oh

(10) Patent No.: US 9,701,732 B2
(45) **Date of Patent: *Jul. 11, 2017**

(54) FUSION PROTEIN COMPRISING ALBUMIN AND RETINOL-BINDING PROTEIN

(71) Applicant: KOREA UNIVERSITY RESEARCH AND BUSINESS FOUNDATION, Seoul (KR)

(72) Inventor: Jun Seo Oh, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/001,720

(22) Filed: Jan. 20, 2016

(65) Prior Publication Data

US 2016/0200796 A1 Jul. 14, 2016

Related U.S. Application Data

(63) Continuation-in-part of application No. 14/002,034, filed as application No. PCT/KR2012/001497 on Feb. 28, 2012, now Pat. No. 9,273,116.

(30) Foreign Application Priority Data

Feb. 28, 2011 (KR) ........................ 10-2011-0018074

(51) Int. Cl.

| | |
|---|---|
| ***C07K 14/76*** | (2006.01) |
| ***C07K 14/435*** | (2006.01) |
| ***C07K 14/765*** | (2006.01) |
| ***A61K 38/17*** | (2006.01) |
| ***C07K 14/47*** | (2006.01) |

(52) U.S. Cl.

CPC ........ *C07K 14/765* (2013.01); *A61K 38/1709* (2013.01); *C07K 14/4702* (2013.01); *C07K 2319/33* (2013.01)

(58) Field of Classification Search

CPC .. A61K 38/1709; C07K 14/435; C07K 14/76; C07K 2319/33; C07K 14/4702; C07K 14/765

See application file for complete search history.

(56) References Cited

U.S. PATENT DOCUMENTS 6,051,692 A 4/2000 Bandman et al.

FOREIGN PATENT DOCUMENTS

| | | | | |
|---|---|---|---|---|
| EP | 2277889 A2 | | 1/2011 | |
| WO | WO 9849301 A1 | * | 11/1998 | .......... C07K 14/705 |
| WO | 2011/015634 A2 | | 2/2011 | |

OTHER PUBLICATIONS

Melanie Childers, A new model of cystic fibrosis pathology: Lack of transport of glutathione and its thiocyanate conjugates, Medical Hypotheses (2006).*

Thomas A. Wynn, Fibrotic Disease and the TH1/TH2 Paradigm, Nat Rev Immunol. Aug. 2004 ; 4(8): 583-594. doi:10.1038.*

Yu-Ru Zhang, Retinoid-Binding Proteins: Similar Protein Architectures Bind Similar Ligands via Completely Different Ways, PLOS, 2012.*

Minoti V Apte, et al; "Dangerous liaisons; Pancreatic stellate cells and pancreatic cancer cells", Journal of Gastroenterology and Hepatology; Mar. 2012; 27 Suppl 2:69-74.

Soyoung Choi, et al; "Recombinatn fusion protein of albumin-retinol binding protein inactivates stellate cells", Biochemical and Biophysical Research Communications; vol. 418, pp. 191-197; Available online Jan. 12, 2012.

Cedric Coulouarn, et al; "Stellate cells and the development of liver cancer: Therapeuti potential of targeting the stroma", Journal of Hepatology, vol. 60, pp. 1306-1309; Jun. 2014.

Nayoung Kim, et al; "Albumin mediates PPAR-γ or C/EBP-α-induced phenotypic changes in pancreatic stellate cells", Biochemical and Biophysical Research Communications; vol. 391 pp. 640-644; Available online Nov. 22, 2009.

Nayoung Kim, et al; "Formation of vitamin A lipid droplets in pancreatic stellate cells requires albumin", Gut; Oct. 2009; vol. 58(10); pp. 1382-1390; Epub Mar. 16, 2009.

Martin Roderfeld, et al; "Inhibition of hepatic fibrogenesis by matrix metallo-proteinase-9 mutants in mice", the FASEB Journal; Mar. 2006; vol. 20(3); pp. 444-454.

Bernd Schnabl, et al; "A TLR4/MD2 fusion protein inhibits LPS-induced pro-inflammatory signalling in hepatic stellate cells", Biochemical and Biophysical Research Communications; vol. 375; pp. 210-214; Available online Aug. 9, 2008.

Alexandra I Thompson, et al; "Hepatic stellate cells: central modulators of hepatic carcinogenesis", BMC Gastroenterology; 15:63; Published May 15, 2015; 13 pages.

Wonbaek Yoo, et al; "Albumin expression is required for adipocyte differentiation of 3T3-L1 cells", Biochemical and Biophysical Research Communications; vol. 397, pp. 170-175; Available online Jun. 1, 2010.

UniProt Protein Database, Protein Accession P02768, Serum Albumin, Accessed on May 29, 2015.

Extended European Search Report dated Jan. 8, 2015; Appln. No. 12752190.4-1410 / 2682406; PCT/KR2012001497.

USPTO RR dated Jan. 5, 2015 in connection with U.S. Appl. No. 14/002,034.

USPTO NFOA dated Jun. 24, 2015 in connection with U.S. Appl. No. 14/002,034.

USPTO NOA mailed Oct. 20, 2015 in connection with U.S. Appl. No. 14/002,034.

(Continued)

*Primary Examiner* — Hasan Ahmed
*Assistant Examiner* — Erinne Dabkowski
(74) *Attorney, Agent, or Firm* — Ladas & Parry LLP; Loren K. Thompson

(57) ABSTRACT

There is provided a fusion protein comprising albumin and retinol-binding protein (RBP), which can be used for preventing or treating fibrotic diseases. The fusion protein, in which albumin and RBP are bound together, is incorporated into stellate cells and induces phenotypic reversion from myofibroblast-like cells to quiescent fat-storing phenotype. Therefore, the fusion protein can be effectively used in preventing or treating fibrotic diseases occurring in the liver, pancreas, lung, or other organs.

18 Claims, 13 Drawing Sheets

(56) References Cited

OTHER PUBLICATIONS

Mert Erkan, et al; "StellaTUM: current consensus and discussion on pancreatic stellate cell research", Gut, Feb. 2012, vol. 61, No. 2, pp. 172-178.

Albert Geerts: "Biology of stellate cells", livr.vub.ac.be/docs/Geerts.pdf; Lab for Cell Biology, Vrije Universiteit Brussel (V.U.B.) Belgium, 1 page.

Virginia Hernandez-Gea et al; "Pathogenesis of Liver Fibrosis", Annu. Rev. Pathol. Mech. Dis.; First published online as a Review in Advance on Nov. 8, 2010; vol. 6, pp. 425-456.

Nina E. Nagy, et al; "Storage of viatmin A in extrahepatic stellate cells in normal rats", Journal of Lipid Research, vol. 38, Apr. 1997, pp. 645-658.

* cited by examiner control albumin

R-III

I-R-III control mutant R-III

SEQUENCE LISTING

```
<160> NUMBER OF SEQ ID NOS: 35

<210> SEQ ID NO 1
<211> LENGTH: 1827
<212> TYPE: DNA
<213> ORGANISM: Homo sapiens

<400> SEQUENCE: 1

atgaagtggg taacctttat ttcccttctt tttctcttta gctcggctta ttccaggggt     60

gtgtttcgtc gagatgcaca caagagtgag gttgctcatc ggtttaaaga tttgggagaa    120

gaaaatttca aagccttggt gttgattgcc tttgctcagt atcttcagca gtgtccattt    180

gaagatcatg taaaattagt gaatgaagta actgaatttg caaaaacatg tgttgctgat    240

gagtcagctg aaaattgtga caaatcactt catacccttt ttggagacaa attatgcaca    300

gttgcaactc ttcgtgaaac ctatggtgaa atggctgact gctgtgcaaa acaagaacct    360

gagagaaatg aatgcttctt gcaacacaaa gatgacaacc caaacctccc ccgattggtg    420

agaccagagg ttgatgtgat gtgcactgct tttcatgaca atgaagagac atttttgaaa    480

aaatacttat atgaaattgc cagaagacat ccttactttt atgccccgga actccttttc    540

tttgctaaaa ggtataaagc tgcttttaca gaatgttgcc aagctgctga taaagctgcc    600

tgcctgttgc caaagctcga tgaacttcgg gatgaaggga aggcttcgtc tgccaaacag    660

agactcaagt gtgccagtct ccaaaaattt ggagaaagag ctttcaaagc atgggcagta    720

gctcgcctga gccagagatt tcccaaagct gagtttgcag aagtttccaa gttagtgaca    780

gatcttacca aagtccacac ggaatgctgc catggagatc tgcttgaatg tgctgatgac    840

agggcggacc ttgccaagta tatctgtgaa aatcaagatt cgatctccag taaactgaag    900
```

```
gaatgctgtg aaaaacctct gttggaaaaa tcccactgca ttgccgaagt ggaaaatgat    960
gagatgcctg ctgacttgcc ttcattagct gctgattttg ttgaaagtaa ggatgtttgc   1020
aaaaactatg ctgaggcaaa ggatgtcttc ctgggcatgt ttttgtatga atatgcaaga   1080
aggcatcctg attactctgt cgtgctgctg ctgagacttg ccaagacata tgaaaccact   1140
ctagagaagt gctgtgccgc tgcagatcct catgaatgct atgccaaagt gttcgatgaa   1200
tttaaacctc ttgtggaaga gcctcagaat ttaatcaaac aaaattgtga gctttttgag   1260
cagcttggag agtacaaatt ccagaatgcg ctattagttc gttacaccaa gaaagtaccc   1320
caagtgtcaa ctccaactct tgtagaggtc tcaagaaacc taggaaaagt gggcagcaaa   1380
tgttgtaaac atcctgaagc aaaaagaatg ccctgtgcag aagactatct atccgtggtc   1440
ctgaaccagt tatgtgtgtt gcatgagaaa acgccagtaa gtgacagagt caccaaatgc   1500
tgcacagaat ccttggtgaa caggcgacca tgcttttcag ctctggaagt cgatgaaaca   1560
tacgttccca aagagtttaa tgctgaaaca ttcaccttcc atgcagatat atgcacactt   1620
tctgagaagg agagacaaat caagaaacaa actgcacttg ttgagctcgt gaaacacaag   1680
cccaaggcaa caaaagagca actgaaagct gttatggatg atttcgcagc ttttgtagag   1740
aagtgctgca aggctgacga taaggagacc tgctttgccg aggagggtaa aaaacttgtt   1800
gctgcaagtc aagctgcctt aggctta                                       1827
```

```
<210> SEQ ID NO 2
<211> LENGTH: 666
<212> TYPE: DNA
<213> ORGANISM: Homo sapiens

<400> SEQUENCE: 2

atgaagtggg taacctttat ttcccttctt tttctcttta gctcggctta ttccaggggt     60
gtgtttcgtc gagatgcaca caagagtgag gttgctcatc ggtttaaaga tttgggagaa    120
gaaaatttca aagccttggt gttgattgcc tttgctcagt atcttcagca gtgtccattt    180
gaagatcatg taaaattagt gaatgaagta actgaatttg caaaaacatg tgttgctgat    240
gagtcagctg aaaattgtga caaatcactt catacccttt ttggagacaa attatgcaca    300
gttgcaactc ttcgtgaaac ctatggtgaa atggctgact gctgtgcaaa acaagaacct    360
gagagaaatg aatgcttctt gcaacacaaa gatgacaacc caaacctccc ccgattggtg    420
agaccagagg ttgatgtgat gtgcactgct tttcatgaca atgaagagac atttttgaaa    480
aaatacttat atgaaattgc cagaagacat ccttactttt atgccccgga actccttttc    540
tttgctaaaa ggtataaagc tgcttttaca gaatgttgcc aagctgctga taaagctgcc    600
tgcctgttgc caaagctcga tgaacttcgg gatgaaggga aggcttcgtc tgccaaacag    660
agactc                                                              666
```

```
<210> SEQ ID NO 3
<211> LENGTH: 612
<212> TYPE: DNA
<213> ORGANISM: Homo sapiens

<400> SEQUENCE: 3

gaagagcctc agaatttaat caaacaaaat tgtgagcttt ttgagcagct tggagagtac     60
aaattccaga atgcgctatt agttcgttac accaagaaag taccccaagt gtcaactcca    120
actcttgtag aggtctcaag aaacctagga aaagtgggca gcaaatgttg taaacatcct    180
gaagcaaaaa gaatgccctg tgcagaagac tatctatccg tggtcctgaa ccagttatgt    240
```

```
gtgttgcatg agaaaacgcc agtaagtgac agagtcacca aatgctgcac agaatccttg    300

gtgaacaggc gaccatgctt ttcagctctg gaagtcgatg aaacatacgt tcccaaagag    360

tttaatgctg aaacattcac cttccatgca gatatatgca cactttctga gaaggagaga    420

caaatcaaga aacaaactgc acttgttgag ctcgtgaaac acaagcccaa ggcaacaaaa    480

gagcaactga aagctgttat ggatgatttc gcagcttttg tagagaagtg ctgcaaggct    540

gacgataagg agacctgctt tgccgaggag ggtaaaaaac ttgttgctgc aagtcaagct    600

gccttaggct ta                                                        612

<210> SEQ ID NO 4
<211> LENGTH: 84
<212> TYPE: DNA
<213> ORGANISM: Homo sapiens

<400> SEQUENCE: 4

atgaagtggg taacctttat ttcccttctt tttctcttta gctcggctta ttccaggggt     60

gtgtttcgtc gagatgcaca caag                                            84

<210> SEQ ID NO 5
<211> LENGTH: 585
<212> TYPE: DNA
<213> ORGANISM: Homo sapiens

<400> SEQUENCE: 5

atgaagtggg tgtgggcgct cttgctgttg gcggcgctgg gcagcggccg cgcggagcgc     60

gactgccgag tgagcagctt ccgagtcaag gagaacttcg acaaggctcg cttctctggg    120

acctggtacg ccatggccaa gaaggacccc gagggcctct ttctgcagga caacatcgtc    180

gcggagttct ccgtggacga gaccggccag atgagcgcca cagccaaggg ccgagtccgt    240

cttttgaata actgggacgt gtgcgcagac atggtgggca ccttcacaga caccgaggac    300

cctgccaagt tcaagatgaa gtactggggc gtagcctcct ttctccagaa aggaaatgat    360

gaccactgga tcgtcgacac agactacgac acgtatgccg tgcagtactc ctgccgcctc    420

ctgaacctcg atggcacctg tgctgacagc tactccttcg tgttttcccg ggaccccaac    480

ggcctgcccc cagaagcgca gaagattgta aggcagcggc aggaggagct gtgcctggcc    540

aggcagtaca ggctgatcgt ccacaacggt tactgcgatg gcaga                    585

<210> SEQ ID NO 6
<211> LENGTH: 531
<212> TYPE: DNA
<213> ORGANISM: Homo sapiens

<400> SEQUENCE: 6

gagcgcgact gccgagtgag cagcttccga gtcaaggaga acttcgacaa ggctcgcttc     60

tctgggacct ggtacgccat ggccaagaag gaccccgagg gcctctttct gcaggacaac    120

atcgtcgcgg agttctccgt ggacgagacc ggccagatga gcgccacagc caagggccga    180

gtccgtcttt tgaataactg ggacgtgtgc gcagacatgg tgggcacctt cacagacacc    240

gaggaccctg ccaagttcaa gatgaagtac tggggcgtag cctcctttct ccagaaagga    300

aatgatgacc actggatcgt cgacacagac tacgacacgt atgccgtgca gtactcctgc    360

cgcctcctga acctcgatgg cacctgtgct gacagctact ccttcgtgtt ttcccgggac    420

cccaacggcc tgcccccaga agcgcagaag attgtaaggc agcggcagga ggagctgtgc    480
```

```
ctggccaggc agtacaggct gatcgtccac aacggttact gcgatggcag a           531


<210> SEQ ID NO 7
<211> LENGTH: 549
<212> TYPE: DNA
<213> ORGANISM: Homo sapiens

<400> SEQUENCE: 7

gagcgcgact gccgagtgag cagcttccga gtcaaggaga acttcgacaa ggctcgcttc     60

tctgggacct ggtacgccat ggccaagaag gaccccgagg gcctctttct gcaggacaac    120

atcgtcgcgg agttctccgt ggacgagacc ggccagatga gcgccacagc caagggccga    180

gtccgtcttt tgaataactg ggacgtgtgc gcagacatgg tgggcacctt cacagacacc    240

gaggaccctg ccaagttcaa gatgaagtac tggggcgtag cctcctttct ccagaaagga    300

aatgatgacc actggatcgt cgacacagac tacgacacgt atgccgtgca gtactcctgc    360

cgcctcctga acctcgatgg cacctgtgct gacagctact ccttcgtgtt ttcccgggac    420

cccaacggcc tgcccccaga agcgcagaag attgtaaggc agcggcagga ggagctgtgc    480

ctggccaggc agtacaggct gatcgtccac aacggttact gcgatggcag atcagaaaga    540

aaccttttg                                                            549


<210> SEQ ID NO 8
<211> LENGTH: 613
<212> TYPE: PRT
<213> ORGANISM: Homo sapiens

<400> SEQUENCE: 8

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Gln Leu
    210                 215                 220
```

```
Glu Arg Asp Cys Arg Val Ser Ser Phe Arg Val Lys Glu Asn Phe Asp
225                 230                 235                 240

Lys Ala Arg Phe Ser Gly Thr Trp Tyr Ala Met Ala Lys Lys Asp Pro
                245                 250                 255

Glu Gly Leu Phe Leu Gln Asp Asn Ile Val Ala Glu Phe Ser Val Asp
            260                 265                 270

Glu Thr Gly Gln Met Ser Ala Thr Ala Lys Gly Arg Val Arg Leu Leu
        275                 280                 285

Asn Asn Trp Asp Val Cys Ala Asp Met Val Gly Thr Phe Thr Asp Thr
    290                 295                 300

Glu Asp Pro Ala Lys Phe Lys Met Lys Tyr Trp Gly Val Ala Ser Phe
305                 310                 315                 320

Leu Gln Lys Gly Asn Asp Asp His Trp Ile Val Asp Thr Asp Tyr Asp
                325                 330                 335

Thr Tyr Ala Val Gln Tyr Ser Cys Arg Leu Leu Asn Leu Asp Gly Thr
            340                 345                 350

Cys Ala Asp Ser Tyr Ser Phe Val Phe Ser Arg Asp Pro Asn Gly Leu
        355                 360                 365

Pro Pro Glu Ala Gln Lys Ile Val Arg Gln Arg Gln Glu Glu Leu Cys
    370                 375                 380

Leu Ala Arg Gln Tyr Arg Leu Ile Val His Asn Gly Tyr Cys Asp Gly
385                 390                 395                 400

Arg Leu Glu Glu Glu Pro Gln Asn Leu Ile Lys Gln Asn Cys Glu Leu
                405                 410                 415

Phe Glu Gln Leu Gly Glu Tyr Lys Phe Gln Asn Ala Leu Leu Val Arg
            420                 425                 430

Tyr Thr Lys Lys Val Pro Gln Val Ser Thr Pro Thr Leu Val Glu Val
        435                 440                 445

Ser Arg Asn Leu Gly Lys Val Gly Ser Lys Cys Cys Lys His Pro Glu
    450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
                485                 490                 495

Lys Cys Cys Thr Glu Ser Leu Val Asn Arg Arg Pro Cys Phe Ser Ala
            500                 505                 510

Leu Glu Val Asp Glu Thr Tyr Val Pro Lys Glu Phe Asn Ala Glu Thr
        515                 520                 525

Phe Thr Phe His Ala Asp Ile Cys Thr Leu Ser Glu Lys Glu Arg Gln
    530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
                565                 570                 575

Val Glu Lys Cys Cys Lys Ala Asp Asp Lys Glu Thr Cys Phe Ala Glu
            580                 585                 590

Glu Gly Lys Lys Leu Val Ala Ala Ser Gln Ala Ala Leu Gly Leu His
        595                 600                 605

His His His His His
    610
```

<210> SEQ ID NO 9
<211> LENGTH: 619

```
<212> TYPE: PRT
<213> ORGANISM: Homo sapiens

<400> SEQUENCE: 9

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Gln Leu Glu Glu
            20                  25                  30

Pro Gln Asn Leu Ile Lys Gln Asn Cys Glu Leu Phe Glu Gln Leu Gly
        35                  40                  45

Glu Tyr Lys Phe Gln Asn Ala Leu Leu Val Arg Tyr Thr Lys Lys Val
    50                  55                  60

Pro Gln Val Ser Thr Pro Thr Leu Val Glu Val Ser Arg Asn Leu Gly
65                  70                  75                  80

Lys Val Gly Ser Lys Cys Cys Lys His Pro Glu Ala Lys Arg Met Pro
                85                  90                  95

Cys Ala Glu Asp Tyr Leu Ser Val Val Leu Asn Gln Leu Cys Val Leu
            100                 105                 110

His Glu Lys Thr Pro Val Ser Asp Arg Val Thr Lys Cys Cys Thr Glu
        115                 120                 125

Ser Leu Val Asn Arg Arg Pro Cys Phe Ser Ala Leu Glu Val Asp Glu
    130                 135                 140

Thr Tyr Val Pro Lys Glu Phe Asn Ala Glu Thr Phe Thr Phe His Ala
145                 150                 155                 160

Asp Ile Cys Thr Leu Ser Glu Lys Glu Arg Gln Ile Lys Lys Gln Thr
                165                 170                 175

Ala Leu Val Glu Leu Val Lys His Lys Pro Lys Ala Thr Lys Glu Gln
            180                 185                 190

Leu Lys Ala Val Met Asp Asp Phe Ala Ala Phe Val Glu Lys Cys Cys
        195                 200                 205

Lys Ala Asp Asp Lys Glu Thr Cys Phe Ala Glu Glu Gly Lys Lys Leu
    210                 215                 220

Val Ala Ala Ser Gln Ala Ala Leu Gly Leu Leu Glu Glu Arg Asp Cys
225                 230                 235                 240

Arg Val Ser Ser Phe Arg Val Lys Glu Asn Phe Asp Lys Ala Arg Phe
                245                 250                 255

Ser Gly Thr Trp Tyr Ala Met Ala Lys Lys Asp Pro Glu Gly Leu Phe
            260                 265                 270

Leu Gln Asp Asn Ile Val Ala Glu Phe Ser Val Asp Glu Thr Gly Gln
        275                 280                 285

Met Ser Ala Thr Ala Lys Gly Arg Val Arg Leu Leu Asn Asn Trp Asp
    290                 295                 300

Val Cys Ala Asp Met Val Gly Thr Phe Thr Asp Thr Glu Asp Pro Ala
305                 310                 315                 320

Lys Phe Lys Met Lys Tyr Trp Gly Val Ala Ser Phe Leu Gln Lys Gly
                325                 330                 335

Asn Asp Asp His Trp Ile Val Asp Thr Asp Tyr Asp Thr Tyr Ala Val
            340                 345                 350

Gln Tyr Ser Cys Arg Leu Leu Asn Leu Asp Gly Thr Cys Ala Asp Ser
        355                 360                 365

Tyr Ser Phe Val Phe Ser Arg Asp Pro Asn Gly Leu Pro Pro Glu Ala
    370                 375                 380

Gln Lys Ile Val Arg Gln Arg Gln Glu Glu Leu Cys Leu Ala Arg Gln
385                 390                 395                 400
```

```
Tyr Arg Leu Ile Val His Asn Gly Tyr Cys Asp Gly Arg Ser Arg Asp
                405                 410                 415

Ala His Lys Ser Glu Val Ala His Arg Phe Lys Asp Leu Gly Glu Glu
            420                 425                 430

Asn Phe Lys Ala Leu Val Leu Ile Ala Phe Ala Gln Tyr Leu Gln Gln
        435                 440                 445

Cys Pro Phe Glu Asp His Val Lys Leu Val Asn Glu Val Thr Glu Phe
    450                 455                 460

Ala Lys Thr Cys Val Ala Asp Glu Ser Ala Glu Asn Cys Asp Lys Ser
465                 470                 475                 480

Leu His Thr Leu Phe Gly Asp Lys Leu Cys Thr Val Ala Thr Leu Arg
                485                 490                 495

Glu Thr Tyr Gly Glu Met Ala Asp Cys Cys Ala Lys Gln Glu Pro Glu
            500                 505                 510

Arg Asn Glu Cys Phe Leu Gln His Lys Asp Asp Asn Pro Asn Leu Pro
        515                 520                 525

Arg Leu Val Arg Pro Glu Val Asp Val Met Cys Thr Ala Phe His Asp
    530                 535                 540

Asn Glu Glu Thr Phe Leu Lys Lys Tyr Leu Tyr Glu Ile Ala Arg Arg
545                 550                 555                 560

His Pro Tyr Phe Tyr Ala Pro Glu Leu Leu Phe Phe Ala Lys Arg Tyr
                565                 570                 575

Lys Ala Ala Phe Thr Glu Cys Cys Gln Ala Ala Asp Lys Ala Ala Cys
            580                 585                 590

Leu Leu Pro Lys Leu Asp Glu Leu Arg Asp Glu Gly Lys Ala Ser Ser
        595                 600                 605

Ala Lys Gln Arg Leu His His His His His His
    610                 615


<210> SEQ ID NO 10
<211> LENGTH: 407
<212> TYPE: PRT
<213> ORGANISM: Homo sapiens

<400> SEQUENCE: 10

Met Lys Trp Val Trp Ala Leu Leu Leu Leu Ala Ala Leu Gly Ser Gly
1               5                   10                  15

Arg Ala Glu Arg Asp Cys Arg Val Ser Ser Phe Arg Val Lys Glu Asn
            20                  25                  30

Phe Asp Lys Ala Arg Phe Ser Gly Thr Trp Tyr Ala Met Ala Lys Lys
        35                  40                  45

Asp Pro Glu Gly Leu Phe Leu Gln Asp Asn Ile Val Ala Glu Phe Ser
    50                  55                  60

Val Asp Glu Thr Gly Gln Met Ser Ala Thr Ala Lys Gly Arg Val Arg
65                  70                  75                  80

Leu Leu Asn Asn Trp Asp Val Cys Ala Asp Met Val Gly Thr Phe Thr
                85                  90                  95

Asp Thr Glu Asp Pro Ala Lys Phe Lys Met Lys Tyr Trp Gly Val Ala
            100                 105                 110

Ser Phe Leu Gln Lys Gly Asn Asp Asp His Trp Ile Val Asp Thr Asp
        115                 120                 125

Tyr Asp Thr Tyr Ala Val Gln Tyr Ser Cys Arg Leu Leu Asn Leu Asp
    130                 135                 140

Gly Thr Cys Ala Asp Ser Tyr Ser Phe Val Phe Ser Arg Asp Pro Asn
```

```
145                 150                 155                 160

Gly Leu Pro Pro Glu Ala Gln Lys Ile Val Arg Gln Arg Gln Glu Glu
                165                 170                 175

Leu Cys Leu Ala Arg Gln Tyr Arg Leu Ile Val His Asn Gly Tyr Cys
            180                 185                 190

Asp Gly Arg Leu Glu Glu Glu Pro Gln Asn Leu Ile Lys Gln Asn Cys
        195                 200                 205

Glu Leu Phe Glu Gln Leu Gly Glu Tyr Lys Phe Gln Asn Ala Leu Leu
    210                 215                 220

Val Arg Tyr Thr Lys Lys Val Pro Gln Val Ser Thr Pro Thr Leu Val
225                 230                 235                 240

Glu Val Ser Arg Asn Leu Gly Lys Val Gly Ser Lys Cys Cys Lys His
                245                 250                 255

Pro Glu Ala Lys Arg Met Pro Cys Ala Glu Asp Tyr Leu Ser Val Val
            260                 265                 270

Leu Asn Gln Leu Cys Val Leu His Glu Lys Thr Pro Val Ser Asp Arg
        275                 280                 285

Val Thr Lys Cys Cys Thr Glu Ser Leu Val Asn Arg Arg Pro Cys Phe
    290                 295                 300

Ser Ala Leu Glu Val Asp Glu Thr Tyr Val Pro Lys Glu Phe Asn Ala
305                 310                 315                 320

Glu Thr Phe Thr Phe His Ala Asp Ile Cys Thr Leu Ser Glu Lys Glu
                325                 330                 335

Arg Gln Ile Lys Lys Gln Thr Ala Leu Val Glu Leu Val Lys His Lys
            340                 345                 350

Pro Lys Ala Thr Lys Glu Gln Leu Lys Ala Val Met Asp Asp Phe Ala
        355                 360                 365

Ala Phe Val Glu Lys Cys Cys Lys Ala Asp Asp Lys Glu Thr Cys Phe
    370                 375                 380

Ala Glu Glu Gly Lys Lys Leu Val Ala Ala Ser Gln Ala Ala Leu Gly
385                 390                 395                 400

Leu His His His His His His
                405


<210> SEQ ID NO 11
<211> LENGTH: 425
<212> TYPE: PRT
<213> ORGANISM: Homo sapiens

<400> SEQUENCE: 11

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Gln Leu Glu Glu
            20                  25                  30

Pro Gln Asn Leu Ile Lys Gln Asn Cys Glu Leu Phe Glu Gln Leu Gly
        35                  40                  45

Glu Tyr Lys Phe Gln Asn Ala Leu Leu Val Arg Tyr Thr Lys Lys Val
    50                  55                  60

Pro Gln Val Ser Thr Pro Thr Leu Val Glu Val Ser Arg Asn Leu Gly
65                  70                  75                  80

Lys Val Gly Ser Lys Cys Cys Lys His Pro Glu Ala Lys Arg Met Pro
                85                  90                  95

Cys Ala Glu Asp Tyr Leu Ser Val Val Leu Asn Gln Leu Cys Val Leu
            100                 105                 110
```

```
His Glu Lys Thr Pro Val Ser Asp Arg Val Thr Lys Cys Cys Thr Glu
        115                 120                 125

Ser Leu Val Asn Arg Arg Pro Cys Phe Ser Ala Leu Glu Val Asp Glu
    130                 135                 140

Thr Tyr Val Pro Lys Glu Phe Asn Ala Glu Thr Phe Thr Phe His Ala
145                 150                 155                 160

Asp Ile Cys Thr Leu Ser Glu Lys Glu Arg Gln Ile Lys Lys Gln Thr
                165                 170                 175

Ala Leu Val Glu Leu Val Lys His Lys Pro Lys Ala Thr Lys Glu Gln
            180                 185                 190

Leu Lys Ala Val Met Asp Asp Phe Ala Ala Phe Val Glu Lys Cys Cys
        195                 200                 205

Lys Ala Asp Asp Lys Glu Thr Cys Phe Ala Glu Glu Gly Lys Lys Leu
    210                 215                 220

Val Ala Ala Ser Gln Ala Ala Leu Gly Leu Leu Glu Glu Arg Asp Cys
225                 230                 235                 240

Arg Val Ser Ser Phe Arg Val Lys Glu Asn Phe Asp Lys Ala Arg Phe
                245                 250                 255

Ser Gly Thr Trp Tyr Ala Met Ala Lys Lys Asp Pro Glu Gly Leu Phe
            260                 265                 270

Leu Gln Asp Asn Ile Val Ala Glu Phe Ser Val Asp Glu Thr Gly Gln
        275                 280                 285

Met Ser Ala Thr Ala Lys Gly Arg Val Arg Leu Leu Asn Asn Trp Asp
    290                 295                 300

Val Cys Ala Asp Met Val Gly Thr Phe Thr Asp Thr Glu Asp Pro Ala
305                 310                 315                 320

Lys Phe Lys Met Lys Tyr Trp Gly Val Ala Ser Phe Leu Gln Lys Gly
                325                 330                 335

Asn Asp Asp His Trp Ile Val Asp Thr Asp Tyr Asp Thr Tyr Ala Val
            340                 345                 350

Gln Tyr Ser Cys Arg Leu Leu Asn Leu Asp Gly Thr Cys Ala Asp Ser
        355                 360                 365

Tyr Ser Phe Val Phe Ser Arg Asp Pro Asn Gly Leu Pro Pro Glu Ala
    370                 375                 380

Gln Lys Ile Val Arg Gln Arg Gln Glu Glu Leu Cys Leu Ala Arg Gln
385                 390                 395                 400

Tyr Arg Leu Ile Val His Asn Gly Tyr Cys Asp Gly Arg Ser Glu Arg
                405                 410                 415

Asn Leu Leu His His His His His His
            420                 425


<210> SEQ ID NO 12
<211> LENGTH: 800
<212> TYPE: PRT
<213> ORGANISM: Homo sapiens

<400> SEQUENCE: 12

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60
```

-continued

```
Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480
```

```
Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu Leu Glu Glu Arg Asp Cys Arg Val Ser Ser Phe Arg Val Lys Glu
    610                 615                 620

Asn Phe Asp Lys Ala Arg Phe Ser Gly Thr Trp Tyr Ala Met Ala Lys
625                 630                 635                 640

Lys Asp Pro Glu Gly Leu Phe Leu Gln Asp Asn Ile Val Ala Glu Phe
                645                 650                 655

Ser Val Asp Glu Thr Gly Gln Met Ser Ala Thr Ala Lys Gly Arg Val
            660                 665                 670

Arg Leu Leu Asn Asn Trp Asp Val Cys Ala Asp Met Val Gly Thr Phe
        675                 680                 685

Thr Asp Thr Glu Asp Pro Ala Lys Phe Lys Met Lys Tyr Trp Gly Val
    690                 695                 700

Ala Ser Phe Leu Gln Lys Gly Asn Asp Asp His Trp Ile Val Asp Thr
705                 710                 715                 720

Asp Tyr Asp Thr Tyr Ala Val Gln Tyr Ser Cys Arg Leu Leu Asn Leu
                725                 730                 735

Asp Gly Thr Cys Ala Asp Ser Tyr Ser Phe Val Phe Ser Arg Asp Pro
            740                 745                 750

Asn Gly Leu Pro Pro Glu Ala Gln Lys Ile Val Arg Gln Arg Gln Glu
        755                 760                 765

Glu Leu Cys Leu Ala Arg Gln Tyr Arg Leu Ile Val His Asn Gly Tyr
    770                 775                 780

Cys Asp Gly Arg Ser Glu Arg Asn Leu Leu His His His His His His
785                 790                 795                 800


<210> SEQ ID NO 13
<211> LENGTH: 788
<212> TYPE: PRT
<213> ORGANISM: Homo sapiens

<400> SEQUENCE: 13

Met Lys Trp Val Trp Ala Leu Leu Leu Leu Ala Ala Leu Gly Ser Gly
1               5                   10                  15

Arg Ala Glu Arg Asp Cys Arg Val Ser Ser Phe Arg Val Lys Glu Asn
            20                  25                  30

Phe Asp Lys Ala Arg Phe Ser Gly Thr Trp Tyr Ala Met Ala Lys Lys
        35                  40                  45

Asp Pro Glu Gly Leu Phe Leu Gln Asp Asn Ile Val Ala Glu Phe Ser
    50                  55                  60
```

```
Val Asp Glu Thr Gly Gln Met Ser Ala Thr Ala Lys Gly Arg Val Arg
65                  70                  75                  80

Leu Leu Asn Asn Trp Asp Val Cys Ala Asp Met Val Gly Thr Phe Thr
                85                  90                  95

Asp Thr Glu Asp Pro Ala Lys Phe Lys Met Lys Tyr Trp Gly Val Ala
            100                 105                 110

Ser Phe Leu Gln Lys Gly Asn Asp Asp His Trp Ile Val Asp Thr Asp
        115                 120                 125

Tyr Asp Thr Tyr Ala Val Gln Tyr Ser Cys Arg Leu Leu Asn Leu Asp
    130                 135                 140

Gly Thr Cys Ala Asp Ser Tyr Ser Phe Val Phe Ser Arg Asp Pro Asn
145                 150                 155                 160

Gly Leu Pro Pro Glu Ala Gln Lys Ile Val Arg Gln Arg Gln Glu Glu
                165                 170                 175

Leu Cys Leu Ala Arg Gln Tyr Arg Leu Ile Val His Asn Gly Tyr Cys
            180                 185                 190

Asp Gly Arg Leu Glu Asp Ala His Lys Ser Glu Val Ala His Arg Phe
        195                 200                 205

Lys Asp Leu Gly Glu Glu Asn Phe Lys Ala Leu Val Leu Ile Ala Phe
    210                 215                 220

Ala Gln Tyr Leu Gln Gln Cys Pro Phe Glu Asp His Val Lys Leu Val
225                 230                 235                 240

Asn Glu Val Thr Glu Phe Ala Lys Thr Cys Val Ala Asp Glu Ser Ala
                245                 250                 255

Glu Asn Cys Asp Lys Ser Leu His Thr Leu Phe Gly Asp Lys Leu Cys
            260                 265                 270

Thr Val Ala Thr Leu Arg Glu Thr Tyr Gly Glu Met Ala Asp Cys Cys
        275                 280                 285

Ala Lys Gln Glu Pro Glu Arg Asn Glu Cys Phe Leu Gln His Lys Asp
    290                 295                 300

Asp Asn Pro Asn Leu Pro Arg Leu Val Arg Pro Glu Val Asp Val Met
305                 310                 315                 320

Cys Thr Ala Phe His Asp Asn Glu Glu Thr Phe Leu Lys Lys Tyr Leu
                325                 330                 335

Tyr Glu Ile Ala Arg Arg His Pro Tyr Phe Tyr Ala Pro Glu Leu Leu
            340                 345                 350

Phe Phe Ala Lys Arg Tyr Lys Ala Ala Phe Thr Glu Cys Cys Gln Ala
        355                 360                 365

Ala Asp Lys Ala Ala Cys Leu Leu Pro Lys Leu Asp Glu Leu Arg Asp
    370                 375                 380

Glu Gly Lys Ala Ser Ser Ala Lys Gln Arg Leu Lys Cys Ala Ser Leu
385                 390                 395                 400

Gln Lys Phe Gly Glu Arg Ala Phe Lys Ala Trp Ala Val Ala Arg Leu
                405                 410                 415

Ser Gln Arg Phe Pro Lys Ala Glu Phe Ala Glu Val Ser Lys Leu Val
            420                 425                 430

Thr Asp Leu Thr Lys Val His Thr Glu Cys Cys His Gly Asp Leu Leu
        435                 440                 445

Glu Cys Ala Asp Asp Arg Ala Asp Leu Ala Lys Tyr Ile Cys Glu Asn
    450                 455                 460

Gln Asp Ser Ile Ser Ser Lys Leu Lys Glu Cys Cys Glu Lys Pro Leu
465                 470                 475                 480
```

```
Leu Glu Lys Ser His Cys Ile Ala Glu Val Glu Asn Asp Glu Met Pro
                485                 490                 495

Ala Asp Leu Pro Ser Leu Ala Ala Asp Phe Val Glu Ser Lys Asp Val
            500                 505                 510

Cys Lys Asn Tyr Ala Glu Ala Lys Asp Val Phe Leu Gly Met Phe Leu
        515                 520                 525

Tyr Glu Tyr Ala Arg Arg His Pro Asp Tyr Ser Val Val Leu Leu Leu
    530                 535                 540

Arg Leu Ala Lys Thr Tyr Glu Thr Thr Leu Glu Lys Cys Cys Ala Ala
545                 550                 555                 560

Ala Asp Pro His Glu Cys Tyr Ala Lys Val Phe Asp Glu Phe Lys Pro
                565                 570                 575

Leu Val Glu Glu Pro Gln Asn Leu Ile Lys Gln Asn Cys Glu Leu Phe
            580                 585                 590

Glu Gln Leu Gly Glu Tyr Lys Phe Gln Asn Ala Leu Leu Val Arg Tyr
        595                 600                 605

Thr Lys Lys Val Pro Gln Val Ser Thr Pro Thr Leu Val Glu Val Ser
    610                 615                 620

Arg Asn Leu Gly Lys Val Gly Ser Lys Cys Cys Lys His Pro Glu Ala
625                 630                 635                 640

Lys Arg Met Pro Cys Ala Glu Asp Tyr Leu Ser Val Val Leu Asn Gln
                645                 650                 655

Leu Cys Val Leu His Glu Lys Thr Pro Val Ser Asp Arg Val Thr Lys
            660                 665                 670

Cys Cys Thr Glu Ser Leu Val Asn Arg Arg Pro Cys Phe Ser Ala Leu
        675                 680                 685

Glu Val Asp Glu Thr Tyr Val Pro Lys Glu Phe Asn Ala Glu Thr Phe
    690                 695                 700

Thr Phe His Ala Asp Ile Cys Thr Leu Ser Glu Lys Glu Arg Gln Ile
705                 710                 715                 720

Lys Lys Gln Thr Ala Leu Val Glu Leu Val Lys His Lys Pro Lys Ala
                725                 730                 735

Thr Lys Glu Gln Leu Lys Ala Val Met Asp Asp Phe Ala Ala Phe Val
            740                 745                 750

Glu Lys Cys Cys Lys Ala Asp Asp Lys Glu Thr Cys Phe Ala Glu Glu
        755                 760                 765

Gly Lys Lys Leu Val Ala Ala Ser Gln Ala Ala Leu Gly Leu His His
    770                 775                 780

His His His His
785
```

<210> SEQ ID NO 14
<211> LENGTH: 1842
<212> TYPE: DNA
<213> ORGANISM: Homo sapiens

<400> SEQUENCE: 14

```
atgaagtggg taacctttat ttcccttctt tttctcttta gctcggctta ttccaggggt      60

gtgtttcgtc gagatgcaca caagagtgag gttgctcatc ggtttaaaga tttgggagaa     120

gaaaatttca aagccttggt gttgattgcc tttgctcagt atcttcagca gtgtccattt     180

gaagatcatg taaaattagt gaatgaagta actgaatttg caaaaacatg tgttgctgat     240

gagtcagctg aaaattgtga caaatcactt catacccttt ttggagacaa attatgcaca     300

gttgcaactc ttcgtgaaac ctatggtgaa atggctgact gctgtgcaaa acaagaacct     360
```

```
gagagaaatg aatgcttctt gcaacacaaa gatgacaacc caaacctccc ccgattggtg    420

agaccagagg ttgatgtgat gtgcactgct tttcatgaca atgaagagac atttttgaaa    480

aaatacttat atgaaattgc cagaagacat ccttactttt atgccccgga actccttttc    540

tttgctaaaa ggtataaagc tgcttttaca gaatgttgcc aagctgctga taaagctgcc    600

tgcctgttgc caaagctcga tgaacttcgg gatgaaggga aggcttcgtc tgccaaacag    660

agactccaat tggagcgcga ctgccgagtg agcagcttcc gagtcaagga gaacttcgac    720

aaggctcgct tctctgggac ctggtacgcc atggccaaga aggaccccga gggcctcttt    780

ctgcaggaca acatcgtcgc ggagttctcc gtggacgaga ccggccagat gagcgccaca    840

gccaagggcc gagtccgtct tttgaataac tgggacgtgt gcgcagacat ggtgggcacc    900

ttcacagaca ccgaggaccc tgccaagttc aagatgaagt actggggcgt agcctccttt    960

ctccagaaag gaaatgatga ccactggatc gtcgacacag actacgacac gtatgccgtg   1020

cagtactcct gccgcctcct gaacctcgat ggcacctgtg ctgacagcta ctccttcgtg   1080

ttttcccggg accccaacgg cctgccccca gaagcgcaga agattgtaag gcagcggcag   1140

gaggagctgt gcctggccag gcagtacagg ctgatcgtcc acaacggtta ctgcgatggc   1200

agactcgagg aagagcctca gaatttaatc aaacaaaatt gtgagctttt tgagcagctt   1260

ggagagtaca aattccagaa tgcgctatta gttcgttaca ccaagaaagt accccaagtg   1320

tcaactccaa ctcttgtaga ggtctcaaga aacctaggaa aagtgggcag caaatgttgt   1380

aaacatcctg aagcaaaaag aatgccctgt gcagaagact atctatccgt ggtcctgaac   1440

cagttatgtg tgttgcatga gaaaacgcca gtaagtgaca gagtcaccaa atgctgcaca   1500

gaatccttgg tgaacaggcg accatgcttt tcagctctgg aagtcgatga aacatacgtt   1560

cccaaagagt ttaatgctga aacattcacc ttccatgcag atatatgcac actttctgag   1620

aaggagagac aaatcaagaa acaaactgca cttgttgagc tcgtgaaaca caagcccaag   1680

gcaacaaaag agcaactgaa agctgttatg gatgatttcg cagcttttgt agagaagtgc   1740

tgcaaggctg acgataagga gacctgcttt gccgaggagg gtaaaaaact tgttgctgca   1800

agtcaagctg ccttaggctt acatcatcat catcatcatt aa                      1842
```

<210> SEQ ID NO 15
<211> LENGTH: 1860
<212> TYPE: DNA
<213> ORGANISM: Homo sapiens

<400> SEQUENCE: 15

```
atgaagtggg taacctttat ttcccttctt tttctcttta gctcggctta ttccaggggt     60

gtgtttcgtc gagatgcaca caagcaattg gaagagcctc agaatttaat caaacaaaat    120

tgtgagcttt ttgagcagct tggagagtac aaattccaga atgcgctatt agttcgttac    180

accaagaaag taccccaagt gtcaactcca actcttgtag aggtctcaag aaacctagga    240

aaagtgggca gcaaatgttg taaacatcct gaagcaaaaa gaatgccctg tgcagaagac    300

tatctatccg tggtcctgaa ccagttatgt gtgttgcatg agaaaacgcc agtaagtgac    360

agagtcacca aatgctgcac agaatccttg gtgaacaggc gaccatgctt ttcagctctg    420

gaagtcgatg aaacatacgt tcccaaagag tttaatgctg aaacattcac cttccatgca    480

gatatatgca cactttctga gaaggagaga caaatcaaga aacaaactgc acttgttgag    540

ctcgtgaaac acaagcccaa ggcaacaaaa gagcaactga aagctgttat ggatgatttc    600
```

```
gcagcttttg tagagaagtg ctgcaaggct gacgataagg agacctgctt tgccgaggag    660
ggtaaaaaac ttgttgctgc aagtcaagct gccttaggct tactcgagga gcgcgactgc    720
cgagtgagca gcttccgagt caaggagaac ttcgacaagg ctcgcttctc tgggacctgg    780
tacgccatgg ccaagaagga ccccgagggc ctctttctgc aggacaacat cgtcgcggag    840
ttctccgtgg acgagaccgg ccagatgagc gccacagcca agggccgagt ccgtcttttg    900
aataactggg acgtgtgcgc agacatggtg ggcaccttca cagacaccga ggaccctgcc    960
aagttcaaga tgaagtactg gggcgtagcc tcctttctcc agaaaggaaa tgatgaccac   1020
tggatcgtcg acacagacta cgacacgtat gccgtgcagt actcctgccg cctcctgaac   1080
ctcgatggca cctgtgctga cagctactcc ttcgtgtttt cccgggaccc caacggcctg   1140
cccccagaag cgcagaagat tgtaaggcag cggcaggagg agctgtgcct ggccaggcag   1200
tacaggctga tcgtccacaa cggttactgc gatggcagat ctagagatgc acacaagagt   1260
gaggttgctc atcggtttaa agatttggga gaagaaaatt tcaaagcctt ggtgttgatt   1320
gcctttgctc agtatcttca gcagtgtcca tttgaagatc atgtaaaatt agtgaatgaa   1380
gtaactgaat ttgcaaaaac atgtgttgct gatgagtcag ctgaaaattg tgacaaatca   1440
cttcataccc tttttggaga caaattatgc acagttgcaa ctcttcgtga aacctatggt   1500
gaaatggctg actgctgtgc aaaacaagaa cctgagagaa atgaatgctt cttgcaacac   1560
aaagatgaca acccaaacct cccccgattg gtgagaccag aggttgatgt gatgtgcact   1620
gcttttcatg acaatgaaga gacatttttg aaaaaatact tatatgaaat tgccagaaga   1680
catccttact tttatgcccc ggaactcctt ttctttgcta aaaggtataa agctgctttt   1740
acagaatgtt gccaagctgc tgataaagct gcctgcctgt tgccaaagct cgatgaactt   1800
cgggatgaag ggaaggcttc gtctgccaaa cagagactcc atcatcatca tcatcattaa   1860
```

<210> SEQ ID NO 16
<211> LENGTH: 1224
<212> TYPE: DNA
<213> ORGANISM: Homo sapiens

<400> SEQUENCE: 16

```
atgaagtggg tgtgggcgct cttgctgttg gcggcgctgg gcagcggccg cgcggagcgc     60
gactgccgag tgagcagctt ccgagtcaag gagaacttcg acaaggctcg cttctctggg    120
acctggtacg ccatggccaa gaaggacccc gagggcctct ttctgcagga caacatcgtc    180
gcggagttct ccgtggacga gaccggccag atgagcgcca cagccaaggg ccgagtccgt    240
cttttgaata actgggacgt gtgcgcagac atggtgggca ccttcacaga caccgaggac    300
cctgccaagt tcaagatgaa gtactggggc gtagcctcct ttctccagaa aggaaatgat    360
gaccactgga tcgtcgacac agactacgac acgtatgccg tgcagtactc ctgccgcctc    420
ctgaacctcg atggcacctg tgctgacagc tactccttcg tgttttcccg ggaccccaac    480
ggcctgcccc cagaagcgca gaagattgta aggcagcggc aggaggagct gtgcctggcc    540
aggcagtaca ggctgatcgt ccacaacggt tactgcgatg gcagactcga ggaagagcct    600
cagaatttaa tcaaacaaaa ttgtgagctt tttgagcagc ttggagagta caaattccag    660
aatgcgctat tagttcgtta caccaagaaa gtaccccaag tgtcaactcc aactcttgta    720
gaggtctcaa gaaacctagg aaaagtgggc agcaaatgtt gtaaacatcc tgaagcaaaa    780
agaatgccct gtgcagaaga ctatctatcc gtggtcctga accagttatg tgtgttgcat    840
gagaaaacgc cagtaagtga cagagtcacc aaatgctgca cagaatcctt ggtgaacagg    900
```

```
cgaccatgct tttcagctct ggaagtcgat gaaacatacg ttcccaaaga gtttaatgct    960

gaaacattca ccttccatgc agatatatgc acactttctg agaaggagag acaaatcaag   1020

aaacaaactg cacttgttga gctcgtgaaa cacaagccca aggcaacaaa agagcaactg   1080

aaagctgtta tggatgattt cgcagctttt gtagagaagt gctgcaaggc tgacgataag   1140

gagacctgct ttgccgagga gggtaaaaaa cttgttgctg caagtcaagc tgccttaggc   1200

ttacatcatc atcatcatca ttaa                                          1224
```

<210> SEQ ID NO 17
<211> LENGTH: 1278
<212> TYPE: DNA
<213> ORGANISM: Homo sapiens

<400> SEQUENCE: 17

```
atgaagtggg taacctttat ttcccttctt tttctcttta gctcggctta ttccaggggt     60

gtgtttcgtc gagatgcaca caagcaattg gaagagcctc agaatttaat caaacaaaat    120

tgtgagcttt ttgagcagct tggagagtac aaattccaga atgcgctatt agttcgttac    180

accaagaaag taccccaagt gtcaactcca actcttgtag aggtctcaag aaacctagga    240

aaagtgggca gcaaatgttg taaacatcct gaagcaaaaa gaatgccctg tgcagaagac    300

tatctatccg tggtcctgaa ccagttatgt gtgttgcatg agaaaacgcc agtaagtgac    360

agagtcacca aatgctgcac agaatccttg gtgaacaggc gaccatgctt ttcagctctg    420

gaagtcgatg aaacatacgt tcccaaagag tttaatgctg aaacattcac cttccatgca    480

gatatatgca cactttctga gaaggagaga caaatcaaga aacaaactgc acttgttgag    540

ctcgtgaaac acaagcccaa ggcaacaaaa gagcaactga aagctgttat ggatgatttc    600

gcagcttttg tagagaagtg ctgcaaggct gacgataagg agacctgctt tgccgaggag    660

ggtaaaaaac ttgttgctgc aagtcaagct gccttaggct tactcgagga gcgcgactgc    720

cgagtgagca gcttccgagt caaggagaac ttcgacaagg ctcgcttctc tgggacctgg    780

tacgccatgg ccaagaagga ccccgagggc ctctttctgc aggacaacat cgtcgcggag    840

ttctccgtgg acgagaccgg ccagatgagc gccacagcca agggccgagt ccgtcttttg    900

aataactggg acgtgtgcgc agacatggtg ggcaccttca cagacaccga ggaccctgcc    960

aagttcaaga tgaagtactg gggcgtagcc tcctttctcc agaaaggaaa tgatgaccac   1020

tggatcgtcg acacagacta cgacacgtat gccgtgcagt actcctgccg cctcctgaac   1080

ctcgatggca cctgtgctga cagctactcc ttcgtgtttt cccgggaccc caacggcctg   1140

cccccagaag cgcagaagat tgtaaggcag cggcaggagg agctgtgcct ggccaggcag   1200

tacaggctga tcgtccacaa cggttactgc gatggcagat cagaaagaaa ccttttgcat   1260

catcatcatc atcattag                                                 1278
```

<210> SEQ ID NO 18
<211> LENGTH: 2403
<212> TYPE: DNA
<213> ORGANISM: Homo sapiens

<400> SEQUENCE: 18

```
atgaagtggg taacctttat ttcccttctt tttctcttta gctcggctta ttccaggggt     60

gtgtttcgtc gagatgcaca caagagtgag gttgctcatc ggtttaaaga tttgggagaa    120

gaaaatttca aagccttggt gttgattgcc tttgctcagt atcttcagca gtgtccattt    180
```

```
gaagatcatg taaaattagt gaatgaagta actgaatttg caaaaacatg tgttgctgat    240

gagtcagctg aaaattgtga caaatcactt catacccttt ttggagacaa attatgcaca    300

gttgcaactc ttcgtgaaac ctatggtgaa atggctgact gctgtgcaaa acaagaacct    360

gagagaaatg aatgcttctt gcaacacaaa gatgacaacc caaacctccc ccgattggtg    420

agaccagagg ttgatgtgat gtgcactgct tttcatgaca atgaagagac atttttgaaa    480

aaatacttat atgaaattgc cagaagacat ccttactttt atgccccgga actccttttc    540

tttgctaaaa ggtataaagc tgcttttaca gaatgttgcc aagctgctga taaagctgcc    600

tgcctgttgc caaagctcga tgaacttcgg gatgaaggga aggcttcgtc tgccaaacag    660

agactcaagt gtgccagtct ccaaaaattt ggagaaagag ctttcaaagc atgggcagta    720

gctcgcctga gccagagatt tcccaaagct gagtttgcag aagtttccaa gttagtgaca    780

gatcttacca aagtccacac ggaatgctgc catggagatc tgcttgaatg tgctgatgac    840

agggcggacc ttgccaagta tatctgtgaa aatcaagatt cgatctccag taaactgaag    900

gaatgctgtg aaaaacctct gttggaaaaa tcccactgca ttgccgaagt ggaaaatgat    960

gagatgcctg ctgacttgcc ttcattagct gctgattttg ttgaaagtaa ggatgtttgc   1020

aaaaactatg ctgaggcaaa ggatgtcttc ctgggcatgt ttttgtatga atatgcaaga   1080

aggcatcctg attactctgt cgtgctgctg ctgagacttg ccaagacata tgaaaccact   1140

ctagagaagt gctgtgccgc tgcagatcct catgaatgct atgccaaagt gttcgatgaa   1200

tttaaacctc ttgtggaaga gcctcagaat ttaatcaaac aaaattgtga gctttttgag   1260

cagcttggag agtacaaatt ccagaatgcg ctattagttc gttacaccaa gaaagtaccc   1320

caagtgtcaa ctccaactct tgtagaggtc tcaagaaacc taggaaaagt gggcagcaaa   1380

tgttgtaaac atcctgaagc aaaaagaatg ccctgtgcag aagactatct atccgtggtc   1440

ctgaaccagt tatgtgtgtt gcatgagaaa acgccagtaa gtgacagagt caccaaatgc   1500

tgcacagaat ccttggtgaa caggcgacca tgcttttcag ctctggaagt cgatgaaaca   1560

tacgttccca aagagtttaa tgctgaaaca ttcaccttcc atgcagatat atgcacactt   1620

tctgagaagg agagacaaat caagaaacaa actgcacttg ttgagctcgt gaaacacaag   1680

cccaaggcaa caaaagagca actgaaagct gttatggatg atttcgcagc ttttgtagag   1740

aagtgctgca aggctgacga taaggagacc tgctttgccg aggagggtaa aaaacttgtt   1800

gctgcaagtc aagctgcctt aggcttactc gaggagcgcg actgccgagt gagcagcttc   1860

cgagtcaagg agaacttcga caaggctcgc ttctctggga cctggtacgc catggccaag   1920

aaggaccccg agggcctctt tctgcaggac aacatcgtcg cggagttctc cgtggacgag   1980

accggccaga tgagcgccac agccaagggc cgagtccgtc ttttgaataa ctgggacgtg   2040

tgcgcagaca tggtgggcac cttcacagac accgaggacc ctgccaagtt caagatgaag   2100

tactggggcg tagcctcctt tctccagaaa ggaaatgatg accactggat cgtcgacaca   2160

gactacgaca cgtatgccgt gcagtactcc tgccgcctcc tgaacctcga tggcacctgt   2220

gctgacagct actccttcgt gttttcccgg gaccccaacg gcctgccccc agaagcgcag   2280

aagattgtaa ggcagcggca ggaggagctg tgcctggcca ggcagtacag gctgatcgtc   2340

cacaacggtt actgcgatgg cagatcagaa agaaaccttt tgcatcatca tcatcatcat   2400

tag                                                                 2403
```

<210> SEQ ID NO 19
<211> LENGTH: 2367

<212> TYPE: DNA
<213> ORGANISM: Homo sapiens

<400> SEQUENCE: 19

```
atgaagtggg tgtgggcgct cttgctgttg gcggcgctgg gcagcggccg cgcggagcgc     60
gactgccgag tgagcagctt ccgagtcaag gagaacttcg acaaggctcg cttctctggg    120
acctggtacg ccatggccaa gaaggacccc gagggcctct ttctgcagga caacatcgtc    180
gcggagttct ccgtggacga gaccggccag atgagcgcca cagccaaggg ccgagtccgt    240
cttttgaata actgggacgt gtgcgcagac atggtgggca ccttcacaga caccgaggac    300
cctgccaagt tcaagatgaa gtactggggc gtagcctcct ttctccagaa aggaaatgat    360
gaccactgga tcgtcgacac agactacgac acgtatgccg tgcagtactc ctgccgcctc    420
ctgaacctcg atggcacctg tgctgacagc tactccttcg tgttttcccg ggaccccaac    480
ggcctgcccc cagaagcgca gaagattgta aggcagcggc aggaggagct gtgcctggcc    540
aggcagtaca ggctgatcgt ccacaacggt tactgcgatg gcagactcga ggatgcacac    600
aagagtgagg ttgctcatcg gtttaaagat ttgggagaag aaaatttcaa agccttggtg    660
ttgattgcct ttgctcagta tcttcagcag tgtccatttg aagatcatgt aaaattagtg    720
aatgaagtaa ctgaatttgc aaaaacatgt gttgctgatg agtcagctga aaattgtgac    780
aaatcacttc ataccctttt tggagacaaa ttatgcacag ttgcaactct tcgtgaaacc    840
tatggtgaaa tggctgactg ctgtgcaaaa caagaacctg agagaaatga atgcttcttg    900
caacacaaag atgacaaccc aaacctcccc cgattggtga gaccagaggt tgatgtgatg    960
tgcactgctt ttcatgacaa tgaagagaca tttttgaaaa aatacttata tgaaattgcc   1020
agaagacatc cttactttta tgccccggaa ctccttttct ttgctaaaag gtataaagct   1080
gcttttacag aatgttgcca agctgctgat aaagctgcct gcctgttgcc aaagctcgat   1140
gaacttcggg atgaagggaa ggcttcgtct gccaaacaga gactcaagtg tgccagtctc   1200
caaaaatttg gagaaagagc tttcaaagca tgggcagtag ctcgcctgag ccagagattt   1260
cccaaagctg agtttgcaga agtttccaag ttagtgacag atcttaccaa agtccacacg   1320
gaatgctgcc atggagatct gcttgaatgt gctgatgaca gggcggacct tgccaagtat   1380
atctgtgaaa atcaagattc gatctccagt aaactgaagg aatgctgtga aaaacctctg   1440
ttggaaaaat cccactgcat tgccgaagtg gaaaatgatg agatgcctgc tgacttgcct   1500
tcattagctg ctgattttgt tgaaagtaag gatgtttgca aaaactatgc tgaggcaaag   1560
gatgtcttcc tgggcatgtt tttgtatgaa tatgcaagaa ggcatcctga ttactctgtc   1620
gtgctgctgc tgagacttgc caagacatat gaaaccactc tagagaagtg ctgtgccgct   1680
gcagatcctc atgaatgcta tgccaaagtg ttcgatgaat ttaaacctct tgtggaagag   1740
cctcagaatt taatcaaaca aaattgtgag ctttttgagc agcttggaga gtacaaattc   1800
cagaatgcgc tattagttcg ttacaccaag aaagtacccc aagtgtcaac tccaactctt   1860
gtagaggtct caagaaacct aggaaaagtg ggcagcaaat gttgtaaaca tcctgaagca   1920
aaaagaatgc cctgtgcaga agactatcta tccgtggtcc tgaaccagtt atgtgtgttg   1980
catgagaaaa cgccagtaag tgacagagtc accaaatgct gcacagaatc cttggtgaac   2040
aggcgaccat gcttttcagc tctggaagtc gatgaaacat acgttcccaa agagtttaat   2100
gctgaaacat tcaccttcca tgcagatata tgcacacttt ctgagaagga gagacaaatc   2160
aagaaacaaa ctgcacttgt tgagctcgtg aaacacaagc ccaaggcaac aaaagagcaa   2220
```

```
ctgaaagctg ttatggatga tttcgcagct tttgtagaga agtgctgcaa ggctgacgat   2280

aaggagacct gctttgccga ggagggtaaa aaacttgttg ctgcaagtca agctgcctta   2340

ggcttacatc atcatcatca tcattaa                                        2367


<210> SEQ ID NO 20
<211> LENGTH: 32
<212> TYPE: DNA
<213> ORGANISM: Artificial Sequence
<220> FEATURE:
<223> OTHER INFORMATION: sense primer for albumin domain I in rat

<400> SEQUENCE: 20

ggggtacccc accatgaagt gggtaacctt tc                                    32


<210> SEQ ID NO 21
<211> LENGTH: 27
<212> TYPE: DNA
<213> ORGANISM: Artificial Sequence
<220> FEATURE:
<223> OTHER INFORMATION: antisense primer for albumin domain I in rat

<400> SEQUENCE: 21

ccccaattgc atcctctgac ggacagc                                          27


<210> SEQ ID NO 22
<211> LENGTH: 27
<212> TYPE: DNA
<213> ORGANISM: Artificial Sequence
<220> FEATURE:
<223> OTHER INFORMATION: sense primer for RBP(55-585) in rat

<400> SEQUENCE: 22

gggcaattgg agcgcgactg cagggtg                                          27


<210> SEQ ID NO 23
<211> LENGTH: 27
<212> TYPE: DNA
<213> ORGANISM: Artificial Sequence
<220> FEATURE:
<223> OTHER INFORMATION: antisense primer for RBP(55-585) in rat

<400> SEQUENCE: 23

cccctcgagt ctgctttgac agtaacc                                          27


<210> SEQ ID NO 24
<211> LENGTH: 27
<212> TYPE: DNA
<213> ORGANISM: Artificial Sequence
<220> FEATURE:
<223> OTHER INFORMATION: sense primer for albumin domain III in rat

<400> SEQUENCE: 24

gggctcgagg aagaacctaa gaacttg                                          27


<210> SEQ ID NO 25
<211> LENGTH: 48
<212> TYPE: DNA
<213> ORGANISM: Artificial Sequence
<220> FEATURE:
<223> OTHER INFORMATION: antisense primer for albumin domain III in rat

<400> SEQUENCE: 25

ggctctagat taatgatgat gatgatgatg ggctaaggct tctttgct                   48
```

<210> SEQ ID NO 26
<211> LENGTH: 30
<212> TYPE: DNA
<213> ORGANISM: Artificial Sequence
<220> FEATURE:
<223> OTHER INFORMATION: sense primer for RBP(1-585) in rat

<400> SEQUENCE: 26
gcggaattcc accatggagt gggtgtgggc 30

<210> SEQ ID NO 27
<211> LENGTH: 27
<212> TYPE: DNA
<213> ORGANISM: Artificial Sequence
<220> FEATURE:
<223> OTHER INFORMATION: antisense primer for RBP(1-585) in rat

<400> SEQUENCE: 27
cccctcgagt ctgctttgac agtaacc 27

<210> SEQ ID NO 28
<211> LENGTH: 32
<212> TYPE: DNA
<213> ORGANISM: Artificial Sequence
<220> FEATURE:
<223> OTHER INFORMATION: sense primer for albumin domain I in mouse

<400> SEQUENCE: 28
ggggtacccc accatgaagt gggtaacctt tc 32

<210> SEQ ID NO 29
<211> LENGTH: 27
<212> TYPE: DNA
<213> ORGANISM: Artificial Sequence
<220> FEATURE:
<223> OTHER INFORMATION: antisense primer for albumin domain I in mouse

<400> SEQUENCE: 29
ccccaattgc attctctgac ggacaga 27

<210> SEQ ID NO 30
<211> LENGTH: 27
<212> TYPE: DNA
<213> ORGANISM: Artificial Sequence
<220> FEATURE:
<223> OTHER INFORMATION: sense primer for albumin domain III in mouse

<400> SEQUENCE: 30
gggctcgagg aagagcctaa gaacttg 27

<210> SEQ ID NO 31
<211> LENGTH: 48
<212> TYPE: DNA
<213> ORGANISM: Artificial Sequence
<220> FEATURE:
<223> OTHER INFORMATION: antisense primer for albumin domain III in mouse

<400> SEQUENCE: 31
ggctctagat taatgatgat gatgatgatg ggctaaggtg tctttgca 48

<210> SEQ ID NO 32
<211> LENGTH: 30
<212> TYPE: DNA
<213> ORGANISM: Artificial Sequence
<220> FEATURE:
<223> OTHER INFORMATION: sense primer for RBP(1-585) in mouse

```
<400> SEQUENCE: 32

gcggaattcc accatggagt gggtgtgggc                                    30


<210> SEQ ID NO 33
<211> LENGTH: 27
<212> TYPE: DNA
<213> ORGANISM: Artificial Sequence
<220> FEATURE:
<223> OTHER INFORMATION: antisense primer for RBP(1-585) in mouse

<400> SEQUENCE: 33

cccctcgagc ctgctttgac agtaacc                                       27


<210> SEQ ID NO 34
<211> LENGTH: 27
<212> TYPE: DNA
<213> ORGANISM: Artificial Sequence
<220> FEATURE:
<223> OTHER INFORMATION: sense primer for RBP(55-585) in mouse

<400> SEQUENCE: 34

gggcaattgg agcgcgactg cagggtg                                       27


<210> SEQ ID NO 35
<211> LENGTH: 27
<212> TYPE: DNA
<213> ORGANISM: Artificial Sequence
<220> FEATURE:
<223> OTHER INFORMATION: antisense primer for RBP(55-585) in mouse

<400> SEQUENCE: 35

cccctcgagc ctgctttgac agtaacc                                       27
```

FUSION PROTEIN COMPRISING ALBUMIN AND RETINOL-BINDING PROTEIN

CROSS-REFERENCE TO RELATED APPLICATION

This application is a continuation-in-part of U.S. application Ser. No. 14/002,034, filed Aug. 28, 2013.

SEQUENCE LISTING

The instant application contains a Sequence Listing which is identical to the sequence listing of the parent application Ser. No. 14/002,034 filed Aug. 28, 2013.

TECHNICAL FIELD

The present invention relates to a fusion protein comprising albumin and retinol-binding protein, which is capable of being used for preventing or treating fibrotic diseases occurring in the liver, pancreas, lung, or other organs.

BACKGROUND ART

Tissue fibrosis leads to fatal defunctionalization of tissues. For example, liver fibrosis progresses to hepatocirrhosis, liver failure and liver cancer, and fibrosis in kidney ultimately leads to end-stage renal failure. Nevertheless, up to now, there have been no drugs for treating fibrotic diseases, and tissue grafting is the only cure available. The reason that there are no anti-fibrotic drugs is because molecular mechanism of fibrogenesis has not been clearly elucidated.

It is widely accepted that activated stellate cells play a key role in the development of fibrosis of liver and pancreas and that they are primarily responsible for the excessive deposition of extracellular matrix proteins such as collagen. It appears that, in addition to the liver, stellate cells are present in extrahepatic organs such as the pancreas, lung, kidney, intestine, spleen, salivary gland, and eye.

The stellate cells are important in controlling retinoid homeostasis in the whole body. Vitamin A (retinol), acquired from diet, is transferred to the liver and taken up by hepatocytes as a chylomicron remnant. It has been suggested that retinol binding protein (RBP) plays a role in the transfer of retinol from hepatocytes to hepatic stellate cells via a RBP receptor STRA6. Vitamin A is then stored as retinyl ester in cytoplasmic fat droplets in stellate cells. The present inventors disclosed that albumin is endogenously expressed in the stellate cells and involved in the formation of vitamin A-containing fat droplets, inhibiting stellate cell activation. The forced expression of albumin led to the phenotypic conversion from activated myofibroblast-like cells to quiescent fat-storing phenotype. (Non-Patent Document 1: Kim N, Yoo W, Lee J, Kim H, Lee H, Kim Y, Kim D, Oh J.* (2009) Formation of vitamin A fat droplets in pancreatic stellate cells requires albumin. Gut 58(10), 1382-90.; Non-Patent Document 2: Kim N, Choi S, Lim C, Lee H, Oh J. (2010) Albumin mediates PPAR-g and C/EBP-a-induced phenotypic changes in pancreatic stellate cells. Biochem. Biophys. Res. Commun. 391(1), 640-44.)

DISCLOSURE

Technical Problem

An object of the present invention is to treat fibrotic diseases via increasing the intracellular levels of full-length albumin or its partial protein (domain), which exerts the anti-fibrotic activity by inhibiting stellate cell activation or inducing aging of stellate cells.

Technical Solution

In order to achieve the above object, an exemplary embodiment of the present invention provides a fusion protein comprising albumin and retinol-binding protein (RBP).

Albumin is a multifunctional plasma protein that is primarily synthesized by liver cells. It contributes to the maintenance of oncotic pressure as well as to transport of hydrophobic molecules. Albumin has three domains, each of which consists of two small sub-domains: A and B. According to a crystallographic analysis, five principal fatty acid binding sites are asymmetrically distributed within the albumin (one in sub-domain IB, one between IA and IIA, two in IIIA, and one in IIIB).

The present inventors hypothesized that albumin endogenously expressed in stellate cells may be involved in maintaining the quiescent vitamin A-storing phenotype by inhibiting stellate cell activation. On the other hand, the present inventors noticed that intravenously injected RBP protein is internalized into stellate cells via receptor-mediated endocytosis. In reference to this point, fusion protein comprising albumin (functional domain) and RBP (targeting domain) was developed and the therapeutic potential of fusion protein was then tested. As a result, when activated stellate cells were transfected with the expression vector encoding fusion protein, cells underwent phenotypic reversion to quiescent fat-storing cells, which was accompanied with the decreased in α-SMA levels, a maker for activated stellate cells. Furthermore, when conditioned medium of 293 cells transfected with the fusion protein expression vector was prepared and added to activated stellate cells, the fusion protein was found to be successfully incorporated into the stellate cells, induce the reappearance of cytoplasmic fat droplets, and reduce α-SMA levels. As previously reported with the mutant albumin, in which three high-affinity fatty acid binding sites (Arg410, Tyr411, and Lys525), located in domain III, were substituted with an alanine residue, the expression of the mutant fusion protein having triple point mutation also produces a senescence phenotype in stellate cells.

According to the present invention, the albumin sequence used for the construction of fusion protein may be derived from any species, but may be preferably derived from humans, in order to avoid a risk of immunogenicity. Albumin may be encoded by a nucleic acid sequence as set forth in SEQ ID NO: 1, but the present invention is not limited thereto.

Since intact high-affinity fatty acid binding sites in albumin protein are required for its anti-fibrotic activity and they are asymmetrically distributed in domain I and domain III, it may be preferable to use domain I and/or domain III as fusion protein component, but the present invention is not limited thereto. Therefore, according to a specific example, the albumin used for the construction of fusion protein may be at least one of an albumin I domain and albumin III domain.

The albumin I domain may be encoded by a nucleic acid sequence (1st to 666th nucleic acids among the nucleic acids encoding albumin) as set forth in SEQ ID NO: 2, but the present invention is not limited thereto.

In addition, the albumin III domain may have a nucleic acid sequence (1216th to 1827th nucleic acids among the nucleic acids encoding albumin) as set forth in SEQ ID NO: 3, but the present invention is not limited thereto.

According to a specific example, in the case of locating the albumin III at a N-terminal side of the fusion protein, an albumin N-terminal including a secretory sequence may be added before the albumin III domain. The albumin N-terminal may be encoded by a nucleic acid sequence as set forth in SEQ ID NO: 4, but the present invention is not limited thereto.

Meanwhile, for the RBP bound to the albumin, the full sequence of the RBP or a part of the full sequence of the RBP may be used, and may be properly selected according to an albumin sequence to be bound or an order of binding with the albumin. The RBP may be encoded by a nucleic acid sequence (1st to 585th nucleic acids among the nucleic acid encoding the RBP) as set forth in SEQ ID NO: 5, a nucleic acid sequence (55th to 585th nucleic acids among the nucleic acid encoding the RBP) as set forth in SEQ ID NO: 6, or a nucleic acid sequence (55th to 603th nucleic acids among the nucleic acid encoding the RBP) as set forth in SEQ ID NO: 7, but the present invention is not limited thereto. For example, since when the RBP is bound to the C-terminal of the albumin, a secretory sequence may not be needed, the RBP peptide encoded by a nucleic acid as set forth in SEQ ID NO: 6 or SEQ ID NO: 7 may be used. In addition, in a case where an albumin domain is again bound to the C-terminal of the RBP, it may be preferable to use a partial peptide of the RBP encoded by a nucleic acid sequence as set forth in SEQ ID NO: 7 rather than the full sequence of the RBP.

According to a preferable specific example, the fusion protein may be albumin I domain-RBP-albumin III, albumin III-RBP-albumin I, RBP-albumin III, albumin III-RBP, an albumin-RBP, or RBP-albumin. The albumin I domain-RBP-albumin III is a type in which the N-terminal of the RBP is bound to the C-terminal of albumin I domain and the albumin III domain is bound to the C-terminal of the RBP. The RBP-albumin III, albumin III-RBP, albumin-RBP, and RBP-albumin are also interpreted in the same way. From the above-mentioned sequence analysis, the present inventors found that the native conformations of albumin and RBP protein are conserved in the fusion protein of the above-mentioned type, and that fatty acid binding and RBP-RBP receptor binding are not affected. Therefore, the fusion protein may have one of the amino acid sequences set forth in SEQ ID NO: 8 to SEQ ID NO: 13, but the present invention is not limited thereto. Specifically, the albumin I domain-RBP-albumin III, albumin III-RBP-albumin I, RBP-albumin albumin III-RBP, albumin-RBP, and RBP-albumin may have amino acid sequences set forth in SEQ ID NO: 8, SEQ ID NO: 9, SEQ ID NO: 10, SEQ ID NO: 11, SEQ ID NO: 12, and SEQ ID NO: 13, respectively. These sequences may include peptide sequence for the proteins to be fused and also amino acid residues generated from the addition of endonuclease restriction site, His tag, and the like.

According to another specific example, wild-type albumin, or the wild-type albumin having partially substituted amino acids, may be used to induce aging of stellate cells by the variation of albumin. According to a specific example, for the albumin or albumin III domain included in the fusion protein, Arg410, Tyr411, and Lys525 may be substituted with Ala, but the present invention is not limited thereto.

In addition, the present invention provides a polynucleotide encoding the above-mentioned fusion protein comprising albumin and RBP, a recombinant vector including the polynucleotide, and a transformant containing the recombinant vector.

According to the present invention, the polynucleotide may have nucleic acid sequences set forth in SEQ ID NO: 14 to SEQ ID NO: 19, but the present invention is not limited thereto. Specifically, albumin I domain-RBP-albumin III, albumin III-RBP-albumin I, RBP-albumin III, albumin III-RBP, albumin-RBP, and RBP-albumin may be respectively encoded by nucleic acid sequences set forth in SEQ ID NO: 14, SEQ ID NO: 15, SEQ ID NO: 16, SEQ ID NO: 17, SEQ ID NO: 18, and SEQ ID NO: 19, but the present invention is not limited thereto. These sequences may include nucleic acids encoding the proteins to be fused, nucleic acids encoding restriction sites used for fusing proteins, a His tag for purifying, a stop codon, and the like.

According to another specific example, wild-type albumin, or the wild-type albumin having a partially substituted amino acid sequence among the amino acid sequences of the domain thereof may be used to induce aging of stellate cells by variation of the albumin. According to a specific example, for the albumin or albumin III domain included in the fusion protein, Arg410, Tyr411, and Lys525 may be substituted by Ala, but the present invention is not limited thereto.

Meanwhile, the recombinant vector including the polynucleotide may be prepared by inserting the polynucleotide into the known expression vector capable of being used for preparing a fusion protein. In the present invention, the term "vector" means a DNA construct including a DNA sequence operably bound to a proper regulatory sequence capable of expressing DNA in a proper host. A vector may be plasmid, phage particles, or simply a potential genome insert. In the case of transforming into a proper host, the vector can be replicated and can function regardless of a host genome, or may be integrated into the genome itself in some cases. Recently, plasmid is a type that is most generally used as a vector, so that in the present specification, "plasmid" and "vector" are used interchangeably. For purposes of the present invention, a plasmid vector is preferably used. A typical plasmid vector capable of being used for these purposes has (a) a replication origin that allows it to be effectively replicated to include hundreds of plasmid vectors per host cell, (b) antibiotic resistance genes allowing the host cell transformed into the plasmid vector to be selected, and (c) a structure including restriction enzyme cleavage sites capable of receiving insertion of an external DNA fragment. Even if there are no proper restriction enzyme cleavage sites, when a synthetic oligonucleotide adaptor or linker according to the general method is used, the vector and external DNA may be easily ligated.

Meanwhile, such a recombinant vector may include an expression vector allowing a His tag to be expressed at the end of a fusion protein in order to effectively isolate and purify a protein.

A host cell may be transformed by using a polynucleotide encoding a fusion protein including albumin and RBP and a recombinant vector including the polynucleotide. The host cell used for expressing a fusion protein according to the present invention may include a cancer cell, but the present invention is not limited thereto.

In addition, the present invention provides a method of producing a fusion protein in which comprises albumin and RBP comprising expressing the fusion protein in which comprises the albumin and RBP from the transformant. The expression of the fusion protein from the transformant may be generally induced through culturing the host cell. The fusion protein comprising the albumin and RBP according to the present invention may be isolated from a culture medium by a known method for purifying a protein because the albumin and RBP themselves have a secretory signal, and thus the fusion protein is secreted out of the cell.

In the present invention, content in connection with genetic engineering technologies will be more clear by the content as disclosed in the document by Sambrook, et al. (Sambrook, et al. Molecular Cloning, A Laboratory Manual, Cold Spring Harbor laboratory Press, Cold Spring Harbor, N.Y. (2001)) and the document by Frederick, et al. (Frederick M. Ausubel et al., Current protocols in molecular biology volume 1, 2, 3, John Wiley & Sons, Inc. (1994)).

In addition, the present invention provides a pharmaceutical composition for preventing or treating fibrotic diseases, in which the composition contains a fusion protein in which comprises albumin and RBP as an effective ingredient; a use of the fusion protein comprising the albumin and RBP for preparing a medicine for preventing or treating fibrotic diseases; and a method for treating fibrotic diseases, comprising administering to a subject in need thereof a therapeutically effective dose of the fusion protein comprising the albumin and RBP.

According to a specific example, the fibrotic disease occurs in the liver, pancreas, lung, kidney, intestine, spleen, salivary gland, or eye, but the present invention is not limited thereto. Examples of the fibrotic disease capable of being prevented or treated by the fusion protein according to the present invention include liver fibrosis, chronic hepatitis, cirrhosis, chemotherapy-associated steatohepatitis (CASH), lung fibrosis, renal fibrosis, renal failure, pancreatic fibrosis, chronic pancreatitis, retinal fibrosis/gliosis, or salivary gland fibrosis.

It has been widely accepted that tumorigenesis is determined not only by malignant cells but also by microenvironment. Targeting the crosstalk between tumors cells and their microenvironment may also represent a promising therapeutic strategy. In vitro and in vivo studies have convincingly demonstrated that there is a close bi-directional interaction between activated, pancreatic stellate cells and pancreatic cancer cells and between activated, hepatic stellate cells and liver cancer cells. This interaction reportedly increases proliferation and migration of cancer cells and facilitates distant metastasis (Cedric Coulouarn et al., *Journal of hepatology,* 2014, vol. 60, pp. 1306-1309; Minoti V Apte et al. *Journal of Gastroenterology and Hepatology,* 2012, vol. 27 Suppl. 2, pp. 69-74; Alexandra I Thompson et al. *BMC Gastroenterology,* 2015, vol. 15, pp. 63).

Therefore, the present invention provides a pharmaceutical composition for preventing or treating a cancer, in which the composition contains a fusion protein in which comprises albumin and RBP as an effective ingredient; a use of the fusion protein comprising the albumin and RBP for preparing a medicine for preventing or treating a cancer; and a method for treating a cancer, comprising administering to a subject in need thereof a therapeutically effective dose of the fusion protein comprising the albumin and RBP.

The cancer includes liver cancer, pancreatic cancer, lung cancer, or kidney cancer, but the present invention is not limited thereto.

The pharmaceutical composition of the present invention may be preferably formulated into a pharmaceutical composition by further including at least one pharmaceutically acceptable carrier for administration in addition to an effective ingredient. Preferably, a liquid solution for an injection is suitable.

For the composition to be formulated in a liquid solution, the pharmaceutically acceptable carrier may include, to be suitable for sterilization and for a living body, saline solution, sterilized water, Ringer's solution, buffered saline, albumin injection solution, dextrose solution, maltodextrin solution, glycerol, ethanol. In combination with at least one of these components, and if necessary, other general additives, such as antioxidant, a buffer solution, and bacteristat may be added. In addition, a form of dose to be injected, such as an aqueous solution, suspension, and an emulsion, may be formulated by further adding diluents, dispersing agents, surfactants, binding agents, and a lubricant. Furthermore, it may be preferably formulated according to a disease or components by using the method disclosed in Remington's Pharmaceutical Science, Mack Publishing Company, Easton 5 PA, as a proper method in the art.

The pharmaceutical composition of the present invention may be administrated in a general way through a route such as intravenous injection, intra-arterial injection, intraperitoneal injection, intramuscular injection, and intrasternal injection.

An effective dose of an effective ingredient of the pharmaceutical composition according to the present invention means the amount required for effectively preventing or treating diseases. Accordingly, the effective dose may be controlled according to various factors such as a type of disease, disease severity, types and contents of the effective ingredient and other ingredients of the composition, a form of administration, an age, body weight, general health conditions, sex and a diet of a patient, an administration time, an administration route, composition secretion rate, a treatment period, and drugs taken concurrently. For example, in the case of the adult, the fusion protein of the present invention may be administrated in doses of 10 ng/kg to 10 g/kg when administrated once a day or several times a day, but the present invention is not limited thereto.

According to the present invention, subjects may be human, orangutan, chimpanzee, mouse, rat, dog, cow, chicken, pig, goat, and sheep, but they are preferably used.

Effects of the Invention

The fusion protein comprising albumin and retinol-binding protein (RBP) according to the present invention can be used for preventing or treating fibrotic diseases occurring in the liver, pancreas, lung, or other organs by inhibiting the activation of stellate cells or by inducing cellular senescence in stellate cells.

BEST MODE

Figure 1A:
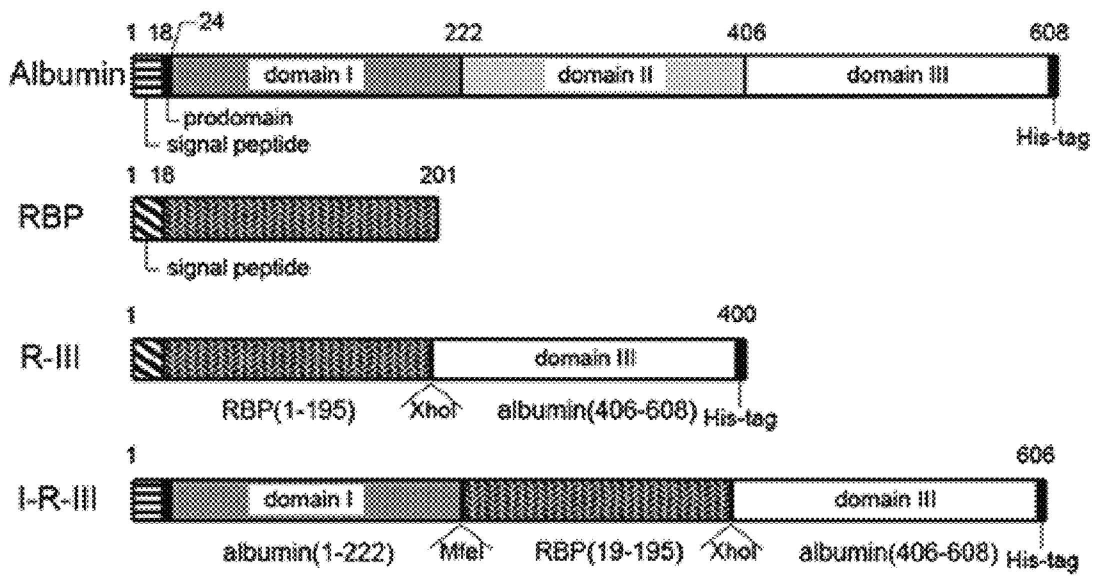
FIG. 1A is a schematic diagram illustrating production of the fusion protein of RBP-albumin$^{406\text{-}608 a.a. (domain\ III)}$ (hereinafter, also referred to as R-III) and albumin$^{1\text{-}222}$$_{(domain\ I)}$-RBP-albumin$^{406\text{-}608}$ (referred to as I-R-III)

The above and other objects, features and advantages of the present invention will become clear by describing Examples below in detail. However, the present invention is not limited to the Examples described below, and can be implemented in various different forms. The following Examples are provided so that this disclosure will completely enable those of ordinary skill in the art to embody and practice the present invention.

EXAMPLE

<Experiment Method>

Isolation and Culture of Pancreatic Stellate Cells (PSCs)

Rat pancreatic stellate cells were isolated according to the method disclosed in Apte, M. V. et al., Periacinar stellate shaped cells in rat pancreas: identification, isolation, and culture. Gut 43 (1), 128-133 (1998). In summary, pancreas was finely minced, placed in a Hank's buffer solution containing 0.05% collagenase, 0.02% protease, and 0.1% DNase, and then shaken at 37° C. for 20 minutes. After filtering through a 150 mm mesh, the cells were centrifuged by 13.2% Nycodenz gradient at 1400 g for 20 minutes. The pancreatic stellate cells were collected from the band just above the interface between the Nycodenz solution and aqueous layer, suspended in a DMEM (Dulbecco's modified Eagle's medium, Carlsbad, Calif.) supplemented with 10% fetal bovine serum, and then plated on a non-coated plastic dish. After reaching confluence in the primary culture, serial passages were obtained always applying 1:3 split.

Constitution of Expression Vector to Albumin-RBP Fusion Protein

Total RNA was extracted from a rat river tissue using a RNeasy kit (Qiagen, Valencia, Calif.) and reverse-transcribed into cDNA using GeneAmp RNA PCR (Applied Biosystems, Foster city, CA). The entire open reading frame (ORF) of albumin or RBP was amplified by polymerase chain reaction (PCR) with the designed primers and inserted into a pBluescript vector.

The expression vector encoding albumin I-RBP-albumin III (referred to as I-R-III) was prepared as follows. A DNA fragment encoding albumin (domain I: 1-666) (SEQ ID NO: 2) or a RBP (55-585) (SEQ ID NO: 6) was amplified from the pBluescript-albumin or pBluescript-RBP by PCR with the primers:

```
Albumin (domain I: 1-666)
                                    (SEQ ID NO: 2)
Sense primer:
                                    (SEQ ID NO: 20)
5' GGGGTACCCC ACCATGAAGT GGGTAACCTT TC 3'

Antisense primer:
                                    (SEQ ID NO: 21)
5' CCCCAATTGC ATCCTCTGAC GGACAGC 3'

RBP (55-585)
                                    (SEQ ID NO: 6)

Sense primer:
                                    (SEQ ID NO: 22)
5' GGGCAATTGG AGCGCGACTG CAGGGTG 3'

Antisense primer:
                                    (SEQ ID NO: 23)
5' CCCCTCGAGT CTGCTTTGAC AGTAACC 3'.
```

The PCR products were double digested with KpnI/MFeI or MfeI/XhoI, respectively, and the DNA fragments purified by an agarose gel electrophoresis were ligated together and then cloned into KpnI/XhoI-cut pBluescript vector to yield pBluescript-I-R.

A DNA fragment encoding albumin (domain III: 1216-1827) (SEQ ID NO: 3) was amplified with the following primers:

```
Sense primer:
                                        (SEQ ID NO: 24)
5' GGGCTCGAGGAAGAACCTAAGAACTTG 3'

Antisense primer:
                                        (SEQ ID NO: 25)
5' GGCTCTAGAT TAATGATGAT GATGATGATGGGCTAAGGCT

TCTTTGCT 3'.
```

A His-tag sequence was included in the antisense primer. The PCR products were double digested with XhoI/XbaI and then ligated with the DNA fragment of I-R prepared above. The resulting DNA fragment I-R-III was inserted into expression vector pcDNA3.1+ at KpnI and XbaI sites to yield pcDNA3.1-I-R-III.

An expression vector encoding RBP-albumin III (referred to as R-III) was prepared as follows. A DNA fragment encoding RBP (1-585) (SEQ ID NO: 5) was amplified with the following primers.

```
Sense primer:
                                   (SEQ ID NO: 26)
5' GCGGAATTCC ACCATGGAGT GGGTGTGGGC 3'

Antisense primer:
                                   (SEQ ID NO: 27)
5' CCCCTCGAGT CTGCTTTGAC AGTAACC 3'
```

The PCR products were double digested with EcoRI/XhoI, ligated with a DNA fragment encoding albumin (domain III: 1216-1827) (SEQ ID NO: 3), and then inserted into pcDNA3.1+ vector at EcoRI and XbaI sites to yield pcDNA3.1-R-III. In the pcDNA3.1-I-R-III or pcDNA3.1-R-III, an albumin/RBP encoding region was located immediately upstream of 6-histidine tag encoding sequence and stop codon in the same reading frame.

Meanwhile, it was reported that the expression of mutant albumin, in which three high-affinity fatty acid binding sites (Arg410, Tyr411, and Lys525) are substituted with an Ala residue, produces a senescence phenotype in stellate cells (Kim N, Yoo W, Lee J, Kim H, Lee H, Kim Y, Kim D, Oh J.* (2009) Formation of vitamin A fat droplets in pancreatic stellate cells requires albumin. *Gut* 58(10), 1382-90). It indicates that direct interaction with lipophilic substances is important for the action of albumin in stellate cells. Accordingly, in the present invention, the expression vector for mutant fusion protein having triple point mutation (R410A/Y411A/K525A) was prepared by a PCR-based method using Muta-Direct™ Site-Directed Mutagenesis Kit (iNtRON, Korea); the expression vector was transfected into the activated stellate cells; and then phenotypic changes were examined.

All the constructs were sequenced by using an auto-sequencer to confirm an albumin/RBP encoding region.

Purification of (his) 6 Tagged Recombinant Fusion Protein

An expression vector encoding mouse R-III was prepared in the same manner as the rat fusion protein. Primers used for a PCR were as follows.

```
Albumin (domain III: 1216-1827)
                                        (SEQ ID NO: 3)

Sense primer:
                                        (SEQ ID NO: 28)
5' GGGCTCGAGG AAGAGCCTAA GAACTTG 3'
```

-continued

```
Antisense primer:
                                        (SEQ ID NO: 29)
5' GGCTCTAGAT TAATGATGAT GATGATGATGGGCTAAGGTG

TCTTTGCA 3'

RBP (1-585)
                                        (SEQ ID NO: 5)

Sense primer:
                                        (SEQ ID NO: 30)
5' GCGGAATTCC ACCATGGAGT GGGTGTGGGC 3'

Antisense primer:
                                        (SEQ ID NO: 31)
5' CCCCTCGAGC CTGCTTTGAC AGTAACC 3'
```

293 cells were stably transfected with an expression vector encoding mouse R-III, and the high expressing, clonal cell lines were selected by assessing levels of secreted R-III by western blotting using an anti-His tag antibody. Culture medium of 293 cells was fractionated with ammonium sulfate (55%), then subject to His Trap affinity column. The sample was further purified by a Resource Q. The purified proteins were dialyzed with deionized water, freeze-dried, and then dissolved in saline solution. As determined by SDS-PAGE and protein staining, the purity of R-III was above 95%.

Transfection

Activated pancreas stellate cells (after passage 2) was transiently transfected using lipofectamine 2000 (Invitrogen, Carlsbad, Calif.), and then after 24 hours, the cells were analyzed.

Western Blotting Analysis

The cells were rinsed in ice-cold phosphate buffer saline (PBS) twice, and harvested by scraping in a lysis buffer solution. The equivalent amounts of proteins were separated by a SDS-PAGE, followed by immunoblot detection using a primary antibody. The primary antibodies were as follows: albumin (Santa Cruz, Santa Cruz, Calif.), α-SMA (Sigma, St. Louis, Mo.), α-tubulin (Cell signaling, Beverly, Mass.) and Type I collagen (Calbiochem, San Diego, Calif.), His-tag (AB Frontier, Seoul, Korea).

Immunofluroescence Analysis

Pancreatic stellate cells were plated on a glass cover slip coated with gelatin. The samples were fixed with paraformaldehyde, incubated with an albumin antibody (Santa Cruz #sc-58698) overnight at 4° C. in a moist chamber, and reacted with a secondary antibody bound with Alexa Fluor 568. The cells were washed with PBS and mounted onto a slide. The stained cells were visualized by using Zeiss AXIO Imager M1 microscope.

Oil Red O Staining

Fat droplets were visualized by staining the pancreatic stellate cells with oil red O using the method disclosed by Koopman (Koopman, R., Schaart, G., & Hesselink, M. K., Optimisation of oil red O staining permits combination with immunofluorescence and automated quantification of lipids. Histochem Cell Biol 116 (1), 63-68 (2001)). The oil red O was diluted in triethyl phosphate instead of isopropane.

Preparation of Liver Fibrosis Model

For $CCl_4$-induced liver fibrosis study, BALB/c mice were treated with $CCl_4$ (1 ml/kg body weight; 1:1 dilution with mineral oil) or mineral oil as a control by intraperitoneal (i.p.) injection three times per week for 7 weeks. For the determination of therapeutic effects of albumin-RBP fusion protein R-III, $CCl_4$-treated mice were randomly divided into three groups; mice were administered via tail vein injection with saline, albumin (10 μg) or R-III (10 μg) every day during the last 2 weeks of $CCl_4$ treatment. For the assessment of preventive effects of R-III, $CCl_4$-treated mice were randomly divided into two groups and administered with saline or R-III three times per week over a period of 7 weeks. Three to five mineral/saline-treated mice were used as normal controls for each experiment. For the study of liver fibrosis induced by bile duct ligation (BDL), mice were anesthetized intraperitoneally by ketamine and xylazine. After midline laparotomy, the common bile duct was double-ligated and transected between the ligatures. The sham operation was performed similarly without BDL. R-III (0, 1, 5, or 10 μg) was daily administered, beginning on day 7 after BDL, for 2 weeks. All experiments were repeated twice.

Preparation of Kidney Fibrosis Model

UUO (unilateral ureteral obstruction) model was performed by using a BALB/c mouse. In summary, the abdominal cavity of the mouse was opened through a midline incision, and then the left ureter was isolated and tied up. By a similar method, sham-operated animals were subjected to the same surgical operation, but the ureter ligation was not performed. In order to test a therapeutic effect of R-III on improving kidney fibrosis, R-III (10 μg) was daily administrated, beginning on day 6 after blocking, for 7 days through tail vein injection. All mice were sacrificed under anesthesia at day 14 and kidney tissues were weighed and collected for various analysis. The half of the kidney was fixed with 10% buffer formalin in order for a histological study, and the other half was snap-frozen in liquid nitrogen to store at −80° C. in order for extractions of protein and RNA. During the experiment, food intake, water intake, urine volume, body weight levels were measured at the baseline and at the time of sacrifice.

Preparation of Lung Fibrosis Model

For bleomycin-induced pulmonary fibrosis study, BALB/c mice were anesthetized with inhalational isoflurane using isoflurane vaporizer. Bleomycin sulfate was dissolved in filtered phosphate-buffered saline (PBS) solution and applied by intratracheal instillation as a single dose of 0.08 units per mouse. Bleomycin-treated mice were randomly divided into two groups; mice were administered via tail vein injection with saline or R-III (10 μg) daily, beginning on day 7 after bleomycin, for 10 days. Mice were then sacrificed on day 18. Lungs were excised and stored at −80° C. for biochemical assays and in 10% neutral buffered formalin for histological analysis.

Immunohistological Analysis

The section (5 μm thickness) of formalin-fixed, paraffin-embedded liver tissues were prepared, stained with a H&E for a histological analysis and with Sirius red or Masson's trichrome for collagen deposition. In addition, the tissue sections were immunohistochemically stained with Type I collagen (Abeam, Cambridge, UK) antibody. In order to quantify the Sirius red staining, Image J software (NIH) was used.

Statistical Analysis

The results were expressed as mean±standard deviation (SD). A statistical analysis was performed by using t-tests. Comparisons were considered significant at $P<0.05$, and the P values were two-tailed.

<Experimental Result>

Figure 1B:
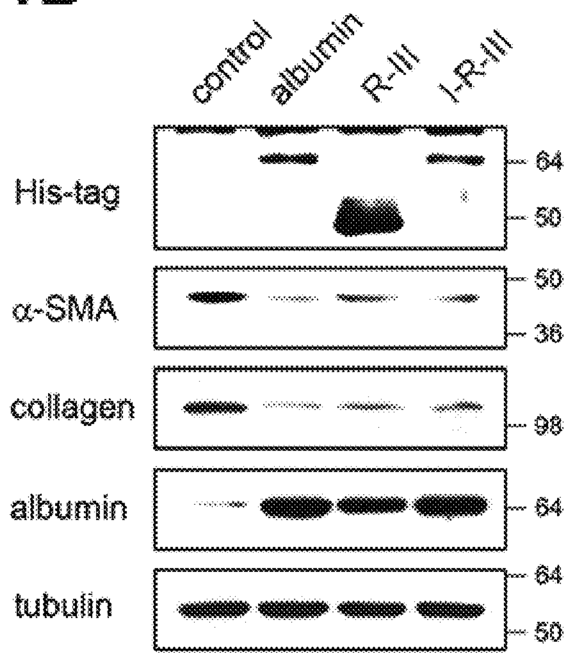
FIG. 1B shows the result of western blot analysis assessing the effect of fusion protein expression on activated stellate cells.

Induction of lipid droplet formation in pancreatic stellate cells by albumin-RBP fusion protein In the aforementioned RBP-albumin$^{406\text{-}608\ a.a.\ (domain\ III)}$ (R-III) and albumin$^{1\text{-}222\ (domain\ I)}$-RBP-albumin$^{406\text{-}608}$ (I-R-III) (FIG. 1A), polyhistidine tag was placed on C-terminal of the fusion proteins to facilitate purification. After pancreatic stellate cells were activated after passage 2, cells were transiently transfected with expression vector for wild-type albumin, R-III or I-R-III and the effects were then examined. Western blotting revealed that fusion proteins have expected size (R-III ~45 kDa and I-R-III ~68 kDa) and decrease the levels of α-SMA and collagen type I, markers of activated stellate cells (FIG. 1B).

Figure 2A:
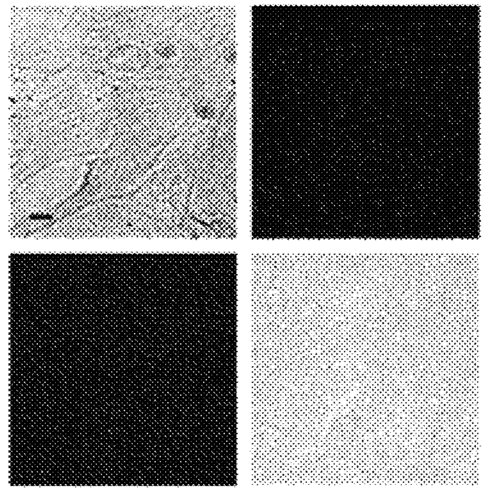
FIGS. 2A to 2D show the effect of the expression of albumin or fusion protein on the morphology of activated stellate cells; phase contrast image (the left top panel), autofluorescence image (the right top panel), immunofluorescence (the left bottom panel), and oil red O staining (the right bottom panel).
Figure 2B:
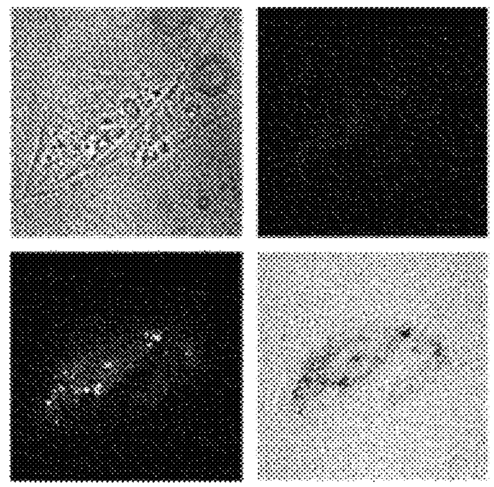
Figure 2C:
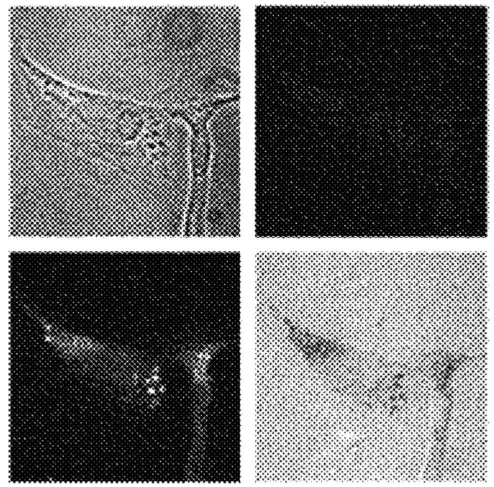
Figure 2D:
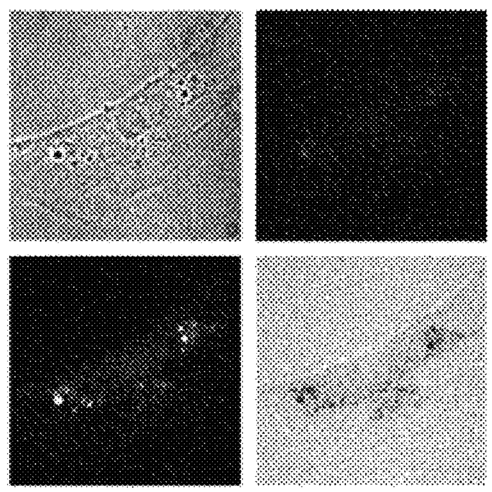

FIGS. 2A to 2D show the morphological changes in stellate cells by the expression of fusion protein; phase contrast image (left top panel), autofluorescens image (right top panel), immunofluorescence (left bottom panel), and oil red O staining (right bottom panel). Activated pancreatic stellate cells under normal culture conditions show a fibroblastoid morphology (FIG. 2A). Expression of wild-type albumin, R-III or I-R-III, however, led to the formation of autofluorescent fat droplets and induced phenotypic changes (FIGS. 2B to 2D), which is consistent with the above-mentioned Western blot data (FIG. 1B). This result suggests that the partial protein (domain III) can still induce stellate cell inactivation similar to the full-length albumin.

Figure 3:
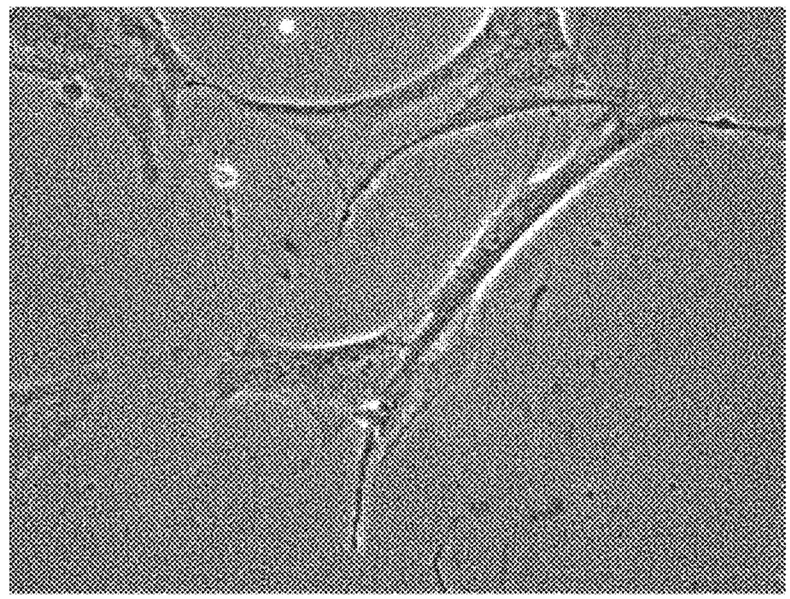
FIG. 3 shows morphological changes in stellate cells transfected with the expression vector for the mutant fusion protein (R-III) having triple point mutation (R410A/Y411A/K525A).
Figure 3:
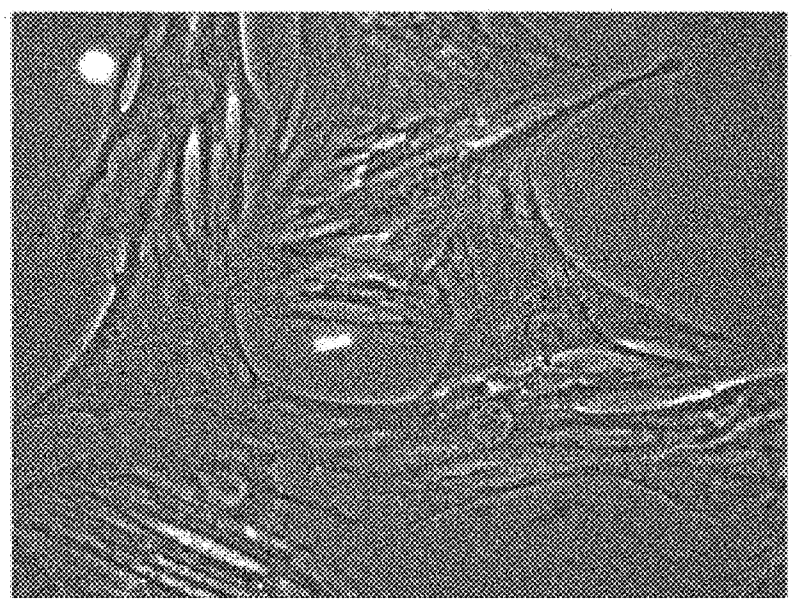

Meanwhile, as a result of experimenting with a mutant fusion protein having triple point mutation (R410A/Y411A/K525A) performed by the above-mentioned method, the expression of the mutant fusion protein produces a senescence phenotype, as manifested by enlarged cell size and flattened cell body (FIG. 3).

Cellular Uptake of Albumin-RBP Fusion Protein into Stellate Cells

Figure 4A:
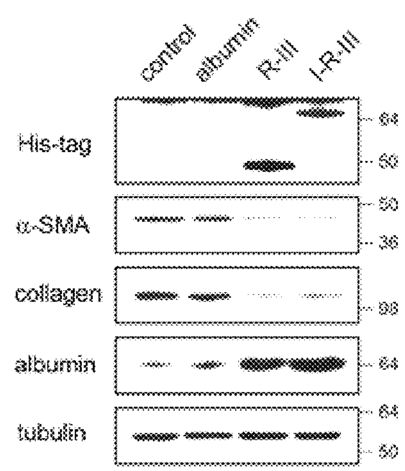
FIG. 4A shows the result of western blot analysis illustrating that the fusion proteins according to the present invention are incorporated into stellate cells and induce biochemical changes.
Figure 4C:
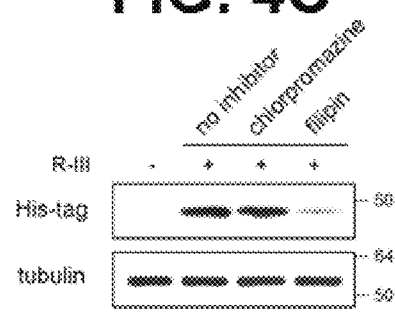
FIG. 4C shows the result of western blot analysis indicating that the fusion protein uptake is mediated through caveolae-mediated endocytosis.
Figure 4B:
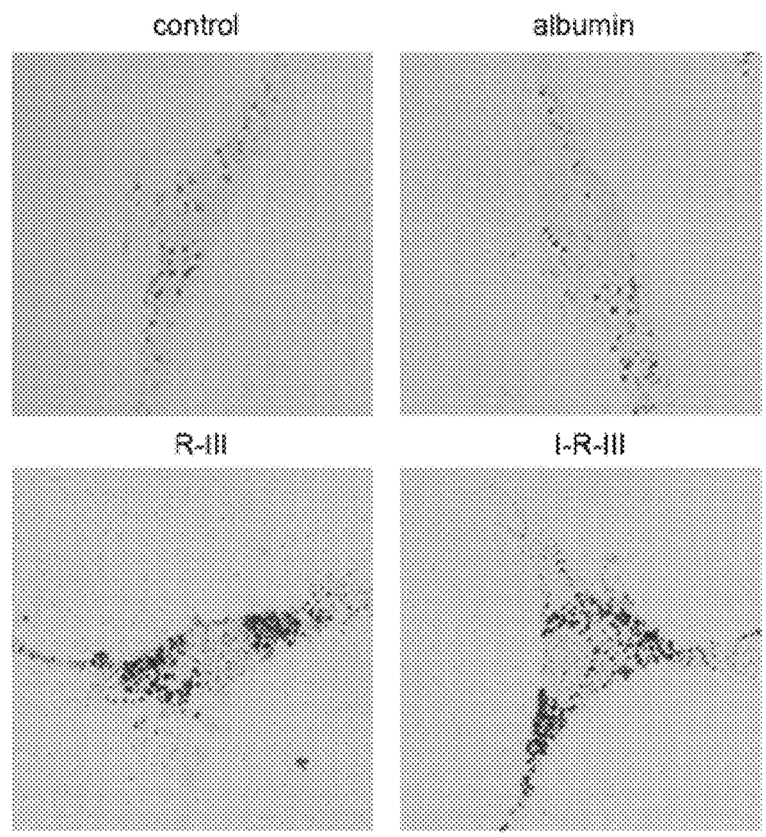
FIG. 4B shows the result of oil red O staining, describing the reappearance of cytoplasmic lipid droplets by fusion protein.

In order to investigate whether the RBP moiety can enable cellular uptake of the fusion protein, conditioned medium was prepared from the 293 cells stably transfected with albumin, R-III, or I-R-III expression vector and applied to activated pancreatic stellate cells. Western blotting with use of anti-His tag antibody revealed that fusion proteins, but not full-length albumin, are successfully incorporated into stellate cells and reduce the levels of α-SMA and collagen type (FIG. 4A). In addition, fusion proteins induced the reappearance of lipid droplets (FIG. 4B). We further investigated the mechanism of R-III internalization using an inhibitor of clathrin-mediated endocytosis (chlorpromazine) or caveolae-mediated endocytosis (filipin). Western blotting analysis revealed that cellular uptake of R-III was largely inhibited by filipin pre-treatment, which is consistent with the previous report that RBP enters the cell through caveolae-mediated endocytosis (FIG. 4C). Therefore, the data shows that each component of the fusion protein is functionally important. In other words, in the fusion protein, the RBP performs a role in stellate cell-targeting moiety and albumin domain performs a role in stellate cell-inactivating domain.

Tissue Distribution of Injected Albumin-RBP Fusion Protein

Figure 5A:
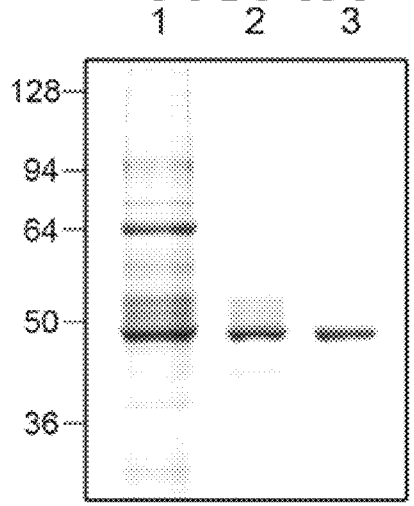
FIG. 5A shows the purification process for the His-tagged, albumin-RBP fusion protein (R-III) according to the present invention using an ammonium sulfate precipitation (lane 1), a His Trap affinity column (lane 2), and a Resource Q column (lane 3)
Figure 5B:
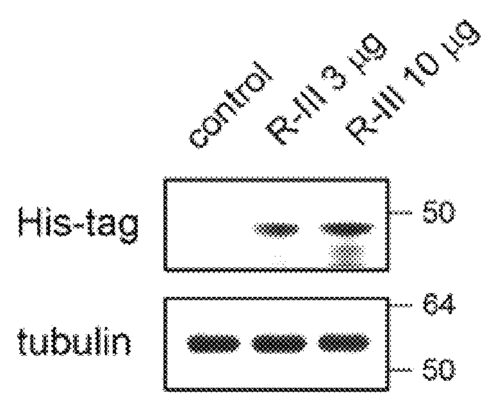
FIG. 5B shows the result of western blot analysis of hepatic tissue lysates after intravenous injection of R-III for 1 week.
Figure 5C:
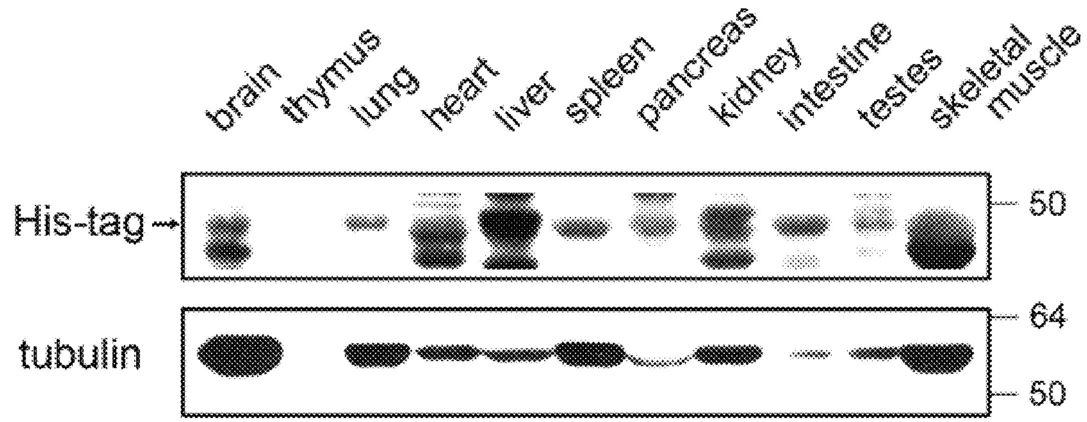
FIG. 5C shows the result of in vivo experiment illustrating tissue distribution of R-III.

Tissue distribution of albumin-RBP fusion protein was investigated in vivo. Since R-III was abundantly expressed and secreted from the transfected 293 cells as compared with I-R-III (data not shown), R-III was selected and purified using FPLC to >95% purity (FIG. 5A). The R-III (3 or 10 μg) dissolved in 0.1 ml of saline solution was injected every day into the tail vein of a BALB/c mouse for 7 days, and then liver lysate was analyzed by western blotting using anti-His tag antibody. The distinct R-III protein band was observed in the R-III-injected mouse, and the band intensity thereof increased in dose dependent manner (FIG. 5B). When equivalent amounts of whole cell lysates obtained from different tissues was analyzed by western blotting, strong R-III signal was observed in liver, and also a weak signal was detected in the brain, lung, spleen, pancreas, kidney, and intestine (FIG. 5C). Such tissue distribution of R-III appears to be similar to that of RBP.

Effect of R-III on Inhibiting Liver Fibrosis

Figure 6A:
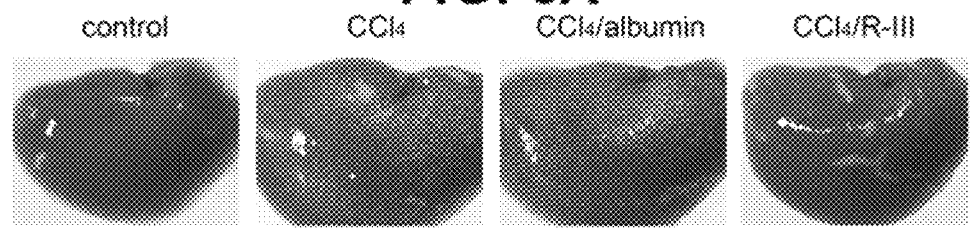
FIG. 6A shows the representative macroscopic pictures of livers from control and $CCl_4$—, $CCl_4$/albumin-, and $CCl_4$/R-III-treated mice.
Figure 6B:
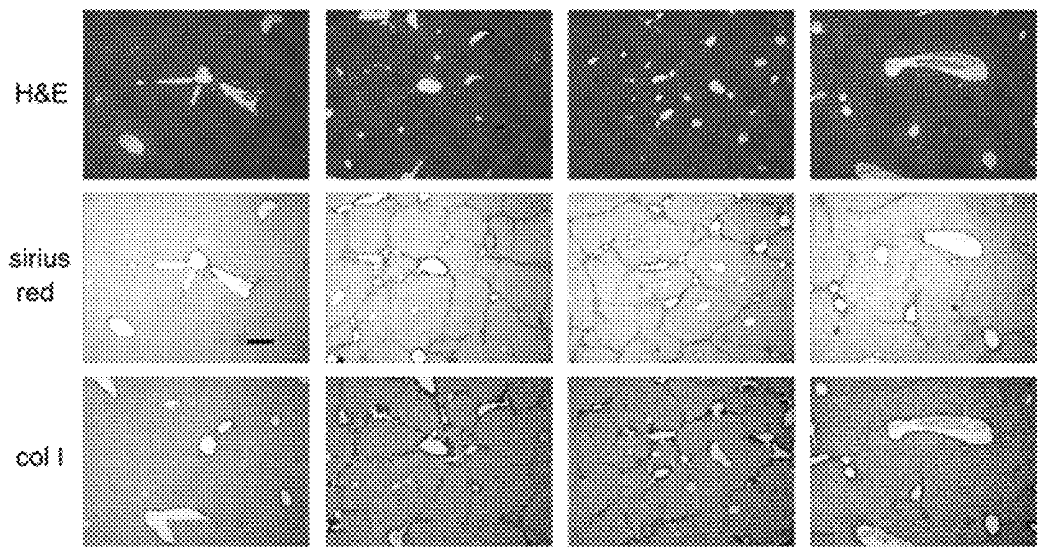
FIG. 6B shows the results of Sirius red staining and immunohistochemical analysis on liver sections for type I collagen (Scale bar, 200 μm).
Figure 7A:
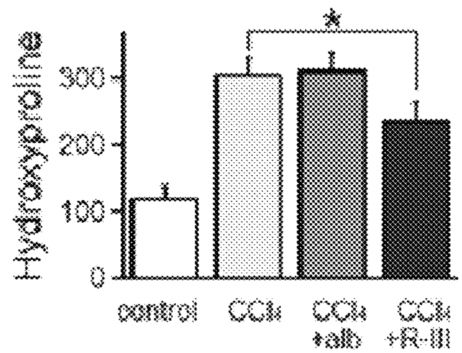
FIG. 7A shows the hydroxyproline content in the livers from control and $CCl_4$—, $CCl_4$/albumin-, and $CCl_4$/R-III-treated mice (μg/g liver) (*P=0.037, two-sample t-test (n=10) ($CCl_4$+R-III compared to $CCl_4$-treated mice))
Figure 7B:
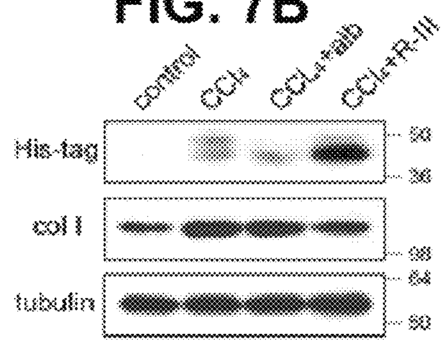
FIG. 7B shows the results of western blot analysis of liver extracts prepared from the treated mice with use of anti-collagen type I antibody.
Figure 7C:
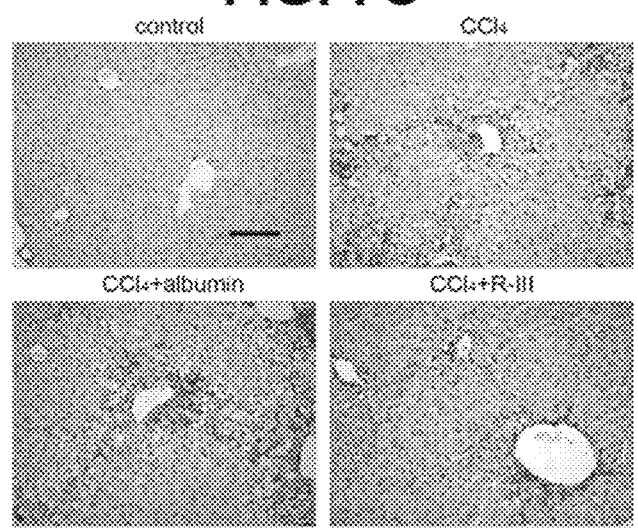
FIG. 7C shows the results of immunohistochemical analysis for α-SMA of liver sections from the treated mice (Scale bar, 200 μm).
Figure 8A:
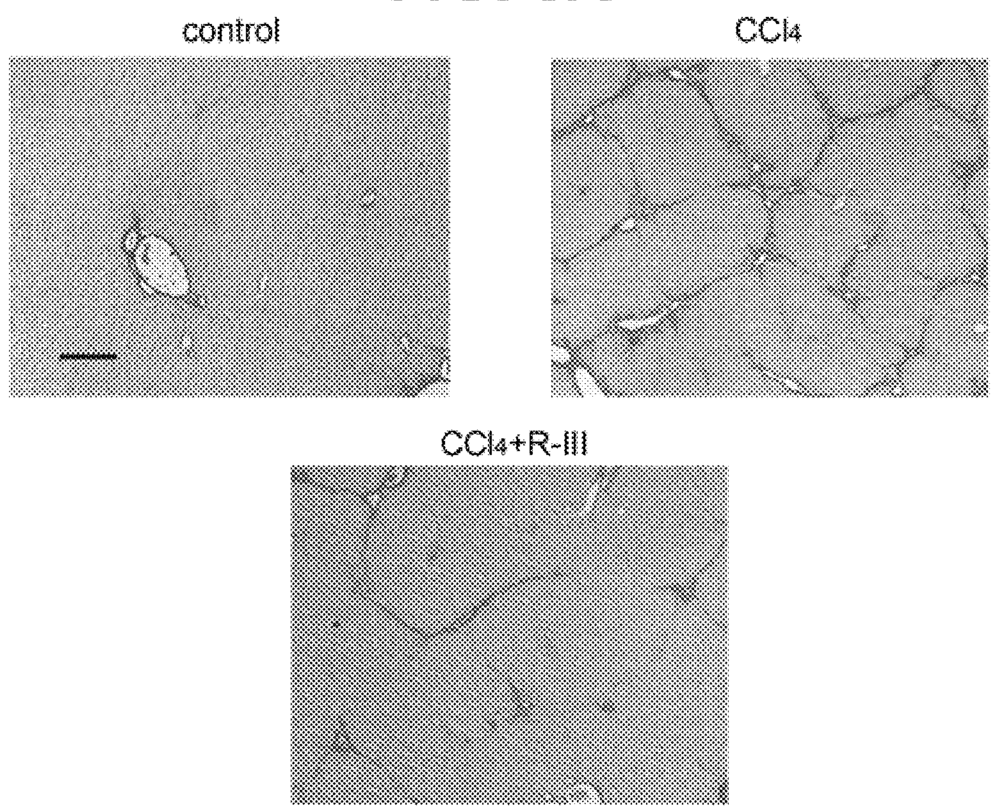
FIG. 8A shows the Sirius red staining results of liver sections from control and $CCl_4$— and $CCl_4$/R-III-treated mice (Scale bar, 200 μm)
Figure 8B:
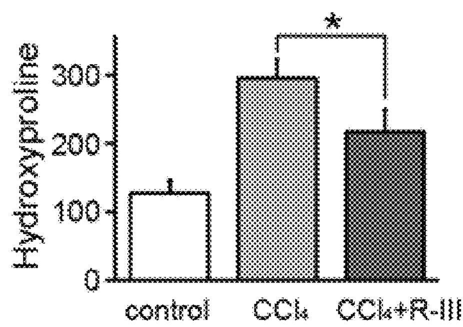
FIG. 8B shows the hydroxyproline content in the livers (μg/g liver) (*P=0.034, two-sample t-test (n=10) (CCl4+R-III compared to $CCl_4$-treated mice)).
Figure 9A:
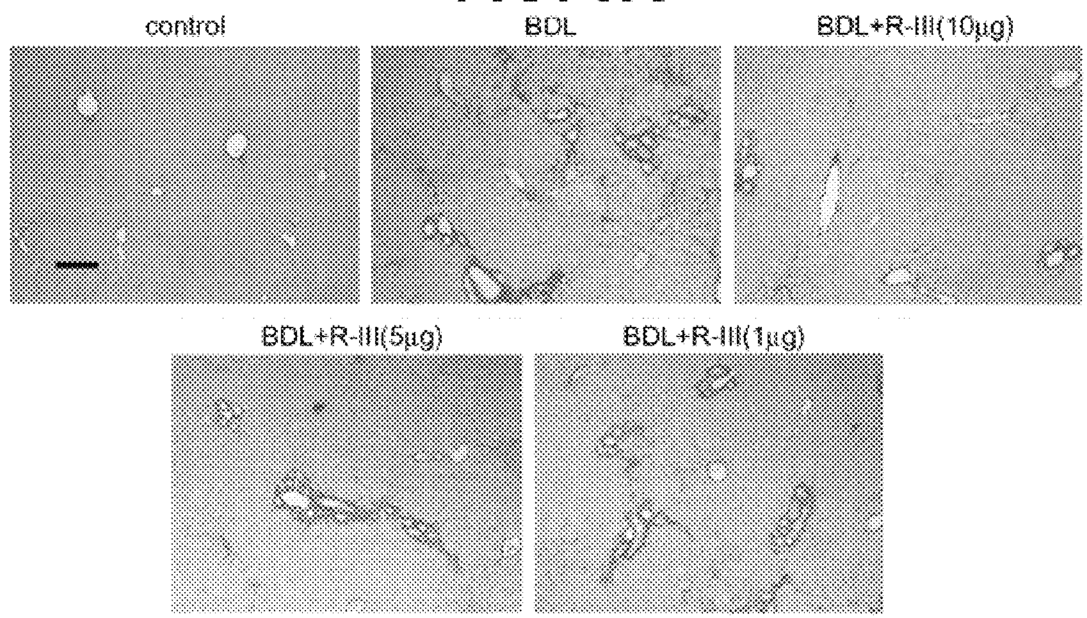
FIG. 9A shows the Sirius red staining results of liver sections from control, bile duct ligation (BDL)-, and BDL/R-III-treated mice (Scale bar, 200 μm)
Figure 9B:
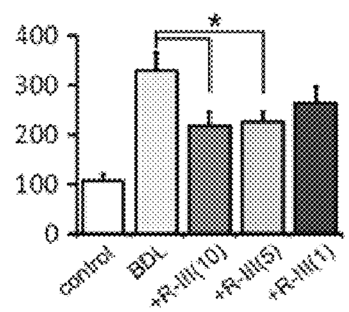
FIG. 9B shows the hydroxyproline content in the livers (μg/g liver) (*P-value, two-sample t-test (n=10) (compared to BDL-treated mice); BDL+R-III (10 μg): 0.031, BDL+R-III (5 μg): 0.026).

On the basis of the in vitro anti-fibrotic activity, we explored the therapeutic effects of R-III on $CCl_4$-induced liver fibrosis model. The external surface of the liver in mineral oil/saline-treated control mice was smooth and glistening, while multiple nodules were found macroscopically on the surfaces of livers in $CCl_4$/saline-treated mice (FIG. 6A). Interestingly, R-III treatment significantly reduced nodule incidence, which was not observed in mice treated with albumin. The histological analysis of livers in the control mice showed normal architecture, whereas liver fibrosis was severe in $CCl_4$/saline-treated mice, as evidenced by disruption of tissue architecture and large fibrous septa formation (FIG. 6B). Sirius red staining and immunohistochemistry also confirmed extensive collagen deposition in the liver (FIG. 6B). R-III significantly reduced histopathological alterations and collagen deposition. Hydroxyproline assays showed 35% reduction in collagen content by R-III, which was also confirmed by Western blot (FIGS. 7A and 7B). Intense immunostaining for α-smooth muscle actin (SMA) was found along the fibrotic septa around the central vein in $CCl_4$/saline-treated livers, and RAH treatment considerably decreased α-SMA staining (FIG. 7C). To examine whether R-III has a preventive effect on $CCl_4$-induced liver fibrosis, mice were treated with $CCl_4$ and R-III on different days three times per week over a period of 7 weeks. Sirius red staining of liver sections showed that R-III treatment markedly reduced collagen deposition (FIG. 8A). Collagen content was reduced by 45% in the R-III-treated group, as measured using hydroxyproline assays (FIG. 8B). Mice underwent bile duct ligation (BDL) and were daily administered with R-III (1, 5 or 10 μg) from 2 to 3 weeks of BDL. R-III treatment reduced cholestatic liver fibrosis (FIG. 9A) and reduced collagen content by up to 45% (FIG. 9B).

Kidney Fibrosis Decrease by R-III

Figure 10A:
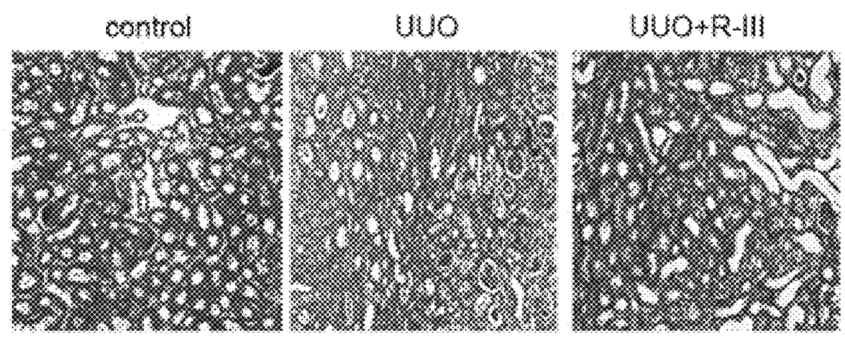
FIG. 10 shows the Masson's trichrome staining (FIG. 10A) and the results of immunohistochemical analysis for TGF-β1 (FIG. 10B) and type I collagen (FIG. 10C) of kidney sections from control, UUO-, and UUO/R-III-treated mice.
Figure 10B:
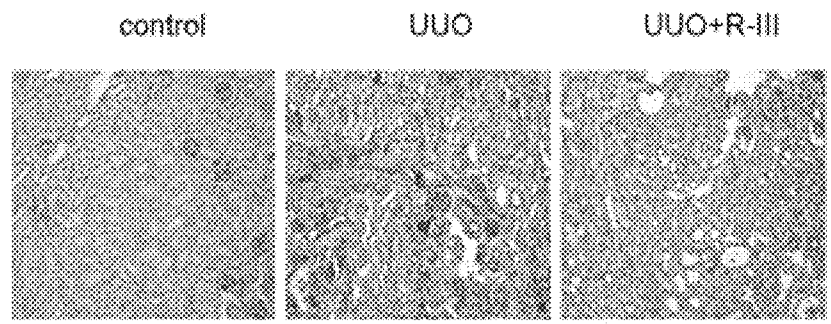
Figure 10C:
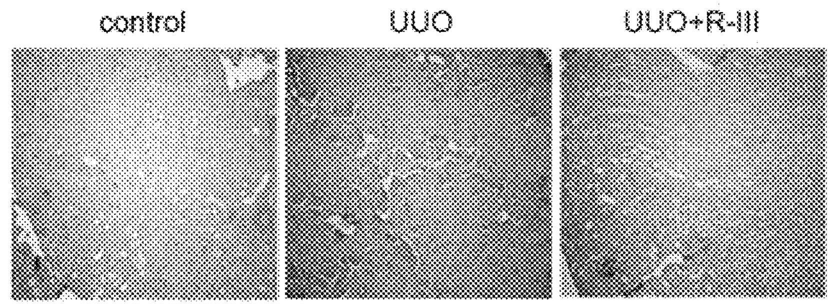
Figure 11A:
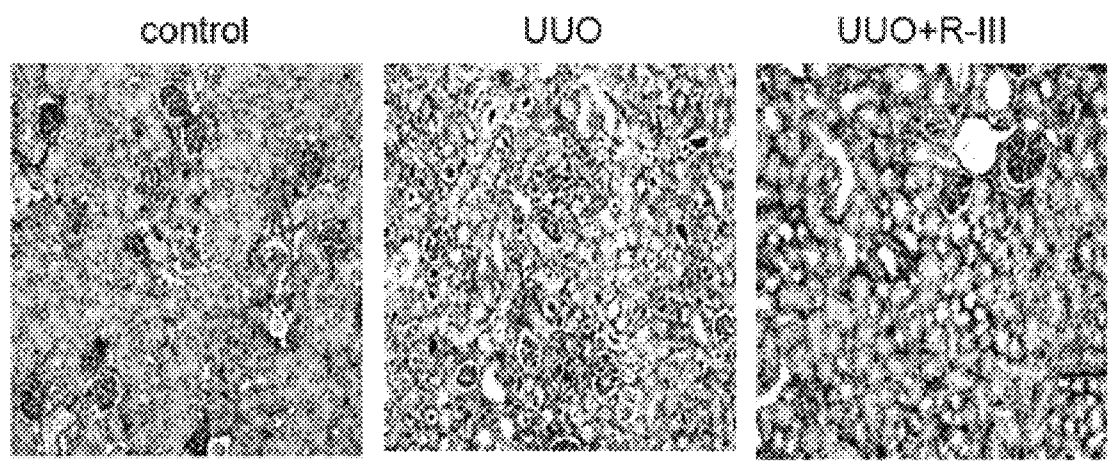
FIG. 11 shows the results of immunohistochemical analysis for desmin (FIG. 11A) and α-SMA (FIG. 11B) of kidney sections from control, UUO-, and UUO/R-III-treated mice.
Figure 11B:
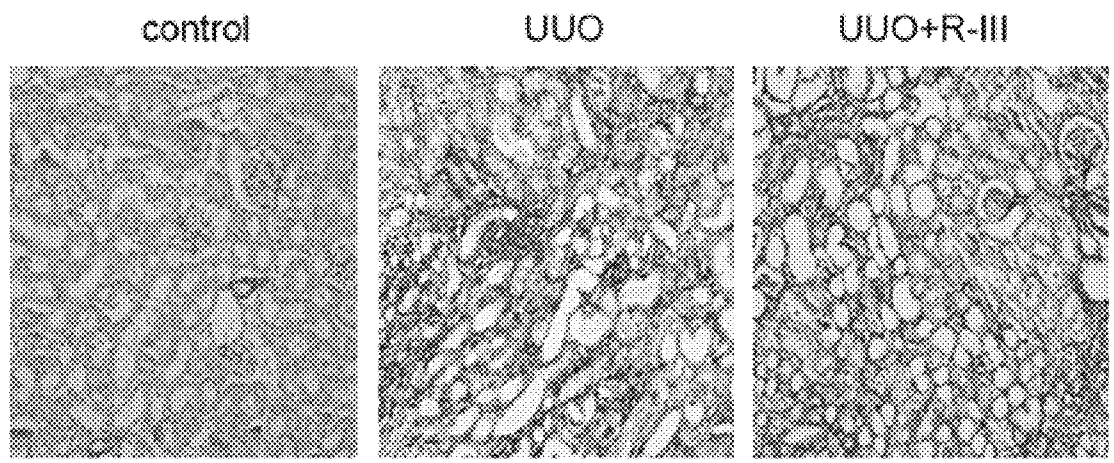

We evaluated the therapeutic effects of R-III against unilateral ureteral obstruction (UUO)-induced renal fibrosis. Sham-operated control mice showed normal renal architecture (FIG. 10). UUO kidneys revealed increased interstitial fibrosis and tubular atrophy, while R-III treatment attenuated the degree of interstitial fibrosis, as evidenced by Masson's trichrome staining (FIG. 10A). Immunoreactivity with pro-fibrotic molecules such as TGF-β1 and collagen type1 was also significantly decreased with R-III treatment (FIGS. 10B and 10C). Immunostaining for α-SMA and desmin, markers of myofibroblast formation, were diminished after R-III treatment compared with those in UUO kidneys (FIGS. 11A and 11B).

Lung Fibrosis Decrease by R-III

Figure 12A:
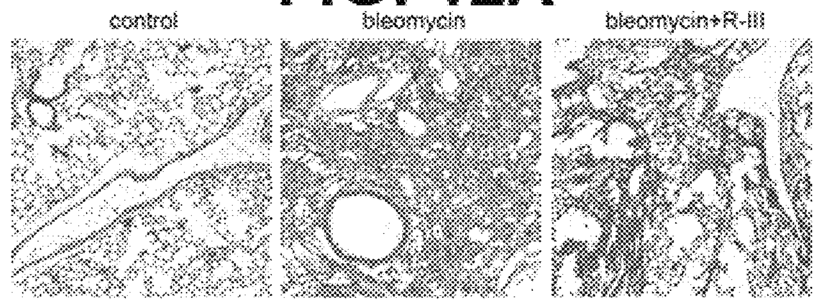
FIG. 12 shows the H&E staining (FIG. 12A) and the results of immunohistochemical analysis for type I collagen (FIG. 12B) of lung sections from control, bleomycin-, and bleomycin/R-III-treated mice.
FIG. 12C shows the hydroxyproline content in the lungs from control and bleomycin-, and bleomycin/R-III-treated mice (μg/g lung).
Figure 12B:
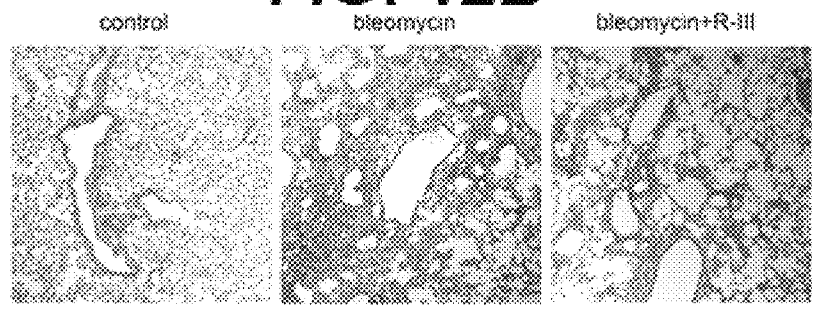
Figure 12C:
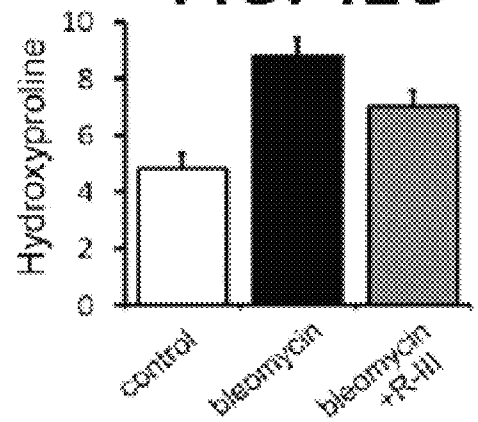
Figure 13A:
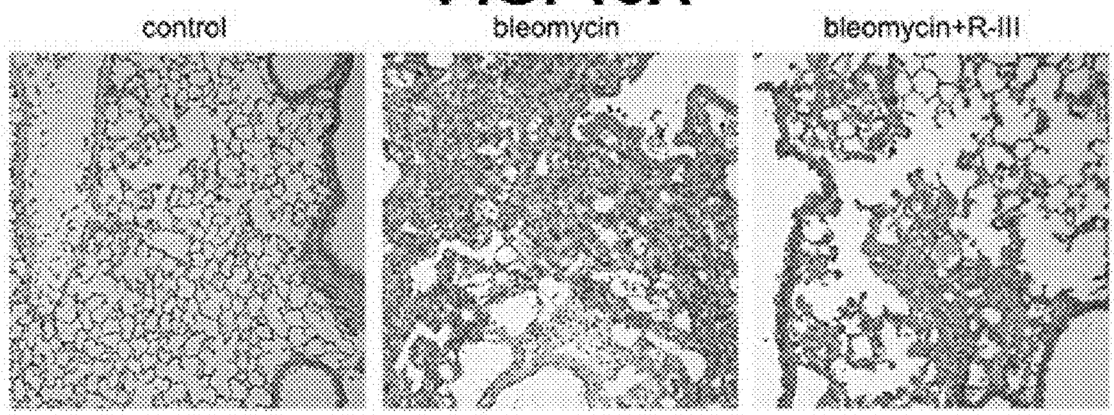
FIG. 13 shows the results of immunohistochemical analysis for α-SMA (FIG. 13A) and TGF-β (FIG. 13B) of lung sections from control, bleomycin-, and bleomycin/R-III-treated mice.
Figure 13B:
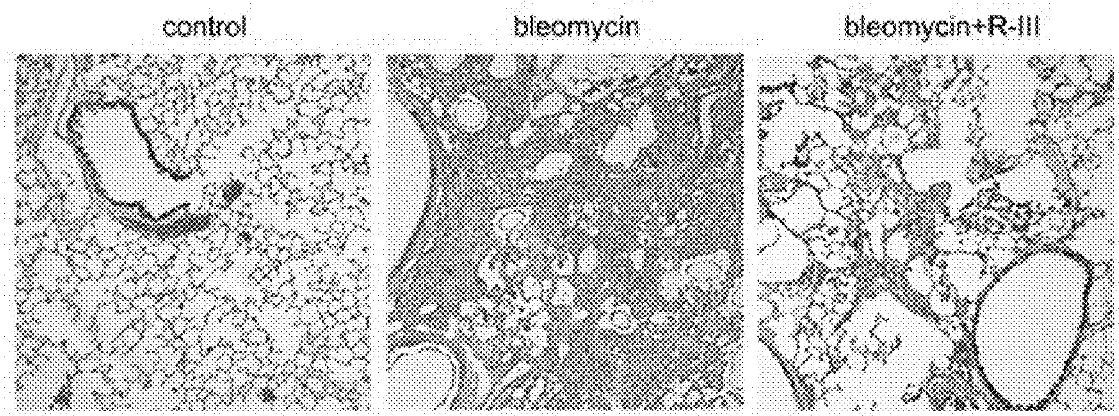

Intratracheal beomycin treatment significantly increased the alveolar septum infiltrates, inflammatory cell infiltrates, and collagen fibers as compared with control group (FIGS. 12A-C). These bleomycin-induced changes were significantly attenuated by R-III treatment. In addition, bleomycin significantly increased levels of lung fibrosis markers α-SMA and TGF-β (FIGS. 13A and 13B). R-III treatment largely reversed bleomycin-induced changes in these lung fibrosis markers. Our results suggest that R-III may have potential therapeutic value for lung fibrosis treatment.

What is claimed is:

1. A method for treating fibrosis, comprising administering to a subject in need thereof a therapeutically effective dose of a fusion protein comprising albumin and a retinol-binding protein (RBP), wherein the fusion protein comprises the sequence selected from the group consisting of SEQ ID NOs: 8 to 13, and wherein the fibrosis occurs in liver, pancreas, lung, kidney, intestine, spleen, salivary gland, or eye.

2. The method of claim 1, wherein the fibrosis occurs in liver, pancreas, lung, or kidney.

3. The method of claim 1, wherein the fibrosis occurs in liver.

4. The method of claim 1, wherein the fibrosis occurs in pancreas.

5. The method of claim 1, wherein the fibrosis occurs in lung.

6. The method of claim 1, wherein the fibrosis occurs in kidney.

7. The method of claim 1, wherein the fusion protein comprises SEQ ID NO: 10.

8. The method of claim 1, wherein the subject is selected from the group consisting of a human, an orangutan, a chimpanzee, a mouse, a rat, a dog, a cow, a chicken, a pig, a goat, and a sheep.

9. The method of claim 1, wherein the subject is a human.

10. A method for treating fibrosis in a subject, the method comprising: administering to the subject a therapeutically effective dose of a fusion protein comprising albumin and a retinol-binding protein (RBP), wherein the fusion protein comprises the sequence selected from the group consisting of SEQ ID NOs. 8 to 13, and wherein the fibrosis is selected from the group consisting of liver fibrosis, pancreas fibrosis, lung fibrosis, or kidney fibrosis.

11. The method of claim 10, wherein the fibrosis is liver fibrosis.

12. The method of claim 10, wherein the fibrosis is pancreas fibrosis.

13. The method of claim 10, wherein the fibrosis is lung fibrosis.

14. The method of claim 10, wherein the fibrosis is kidney fibrosis.

15. The method of claim 10, wherein the fusion protein comprises SEQ ID NO: 10.

16. The method of claim 10, wherein the subject is selected from the group consisting of a human, an orangutan, a chimpanzee, a mouse, a rat, a dog, a cow, a chicken, a pig, a goat, and a sheep.

17. The method of claim 10, wherein the subject is a human.

18. A method for treating liver fibrosis in a human subject, the method comprising: administering to the human subject a therapeutically effective dose of a fusion protein comprising albumin and a retinol-binding protein (RBP), wherein the fusion protein comprises SEQ ID NO: 10.

* * * * *